US012649853B2

(12) United States Patent
Yang et al.

(10) Patent No.: US 12,649,853 B2
(45) Date of Patent: Jun. 9, 2026

(54) LABELS COMPRISING DIBROMOPYRIDAZINEDIONES FOR IMMUNOASSAYS AND METHODS OF PRODUCTION AND USE THEREOF

(71) Applicant: Siemens Healthcare Diagnostics Inc., Tarrytown, NY (US)

(72) Inventors: Yali Yang, Bear, DE (US); David Wen, Northborough, MA (US); Bogdan Draghici, Newark, DE (US); Yi Feng Zheng, Wilmington, DE (US); Raphael Bartz, Newark, DE (US); Qingping Jiang, East Walpole, MA (US); Roland Janzen, Hockessin, DE (US); Joshua Whalen, Landenberg, PA (US); Ling Ngo, Wilmington, DE (US); William Bedzyk, Odessa, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 578 days.

(21) Appl. No.: 18/255,654

(22) PCT Filed: Nov. 10, 2021

(86) PCT No.: PCT/US2021/072319

§ 371 (c)(1),
(2) Date: Jun. 2, 2023

(87) PCT Pub. No.: WO2022/126055

PCT Pub. Date: Jun. 16, 2022

(65) Prior Publication Data

US 2024/0010841 A1 Jan. 11, 2024

Related U.S. Application Data

(60) Provisional application No. 63/122,039, filed on Dec. 7, 2020.

(51) Int. Cl.
*C09B 62/12* (2006.01)
*C07K 16/28* (2006.01)
(Continued)

(52) U.S. Cl.
CPC ............ *C09B 62/125* (2013.01); *C07K 16/28* (2013.01); *G01N 33/582* (2013.01); *G01N 33/6872* (2013.01); *G01N 2333/99* (2013.01)

(58) Field of Classification Search
CPC .................................................. C09B 62/125
See application file for complete search history.

(56) References Cited

U.S. PATENT DOCUMENTS 5,075,218 A 12/1991 Jette et al.
5,538,901 A 7/1996 Law et al.
(Continued)

FOREIGN PATENT DOCUMENTS

WO 2006058287 6/2006

OTHER PUBLICATIONS

Greene Michelle K. et al:“Refined construction of antibody-targeted nanoparticles leads to superior antigen binding and enhanced delivery of an entrapped payload to pancreatic cancer cells”, May 14, 2020.

(Continued)

*Primary Examiner* — Karl J Puttlitz

(57) ABSTRACT

Labels that include dibromopyridazinedione attached to signal molecules are disclosed, along with methods of producing and using same. Also disclosed are conjugates of the label attached to an analyte-specific binder, as well as methods of producing and using same. Kits containing the labels and/or conjugates are also disclosed, along with microfluidics devices containing same.

20 Claims, 12 Drawing Sheets

CA19-9 MAb MCC-HEG-DMAE

CA19-9 MAb-TEG-TSPAE

(51) Int. Cl.
*G01N 33/58* (2006.01)
*G01N 33/68* (2006.01)

(56) References Cited

U.S. PATENT DOCUMENTS

| | | | |
|---|---|---|---|
| 5,565,570 | A | 10/1996 | Mattingly et al. |
| 2009/0286329 | A1 | 11/2009 | Adamczyk et al. |
| 2009/0318627 | A1 | 12/2009 | Natrajan et al. |
| 2015/0031861 | A1 | 1/2015 | Smith et al. |

OTHER PUBLICATIONS

Natrajan Anand et al. "Effect of surfactants on the chemiluminescence of acridinium dimethylphenyl ester labels and their conjugates", Organic & Biomolecular Chemistry, Dec. 31, 2011.
Shijing et al.: "Clinical Immunology"; Medicine Science and Technology Press, China; pp. 158-159, Jan. 31, 2020.
Stefanucci et al: "Fluorescent-labeled bioconjugates of the opioid peptides biphalin and DPDPE incorporating fluorescein-maleimide linkers", Future Medicinal Chemistry, vol. 9, No. 9, Jun. 1, 2017 (Jun. 1, 2017), pp. 859-869.
Zhang, Libin et al: "Site-selective in situ growth of fluorescent polymer• antibody conjugates with enhanced antigen detection by signal amplification", Biomaterials, vol. 64, Sep. 1, 2015 (Sep. 1, 2015), pp. 2-9.
Stefanucci et al: "Developing Cyclic Opioid Analogues: Fluorescently Labeled Bioconjugates of Biphalin", ACS Medicinal Chemistry Letters, vol. 11, No. 5, Jan. 8, 2020 (Jan. 8, 2020), pp. 720-726.
Moody, Paul et al: "Bromomaleimide-Linked Bioconjugates Are Cleavable in Mammalian Cells", Chembiochem, John Wiley & Sons, Hoboken, USA, vol. 13, No. 1, Nov. 18, 2011 (Nov. 18, 2011), pp. 39-41.
Ruirui et al: "Bioconjugation and Fluorescence Labeling of Iron Oxide Nanoparticles Grafted with Bromomaleimide-Terminal Polymers", Biomacromolecules, vol. 19, No. 11, Oct. 11, 2018 (Oct. 11, 2018), pp. 4423-4429.
Hagge, Laurel M. et al: "Intracellular delivery of virus. like particles using a sheddable linker", Journal of Materials Chemistry. B, [Online] vol. 11, No. 30, Jun. 27, 2023 (Jun. 27, 2023) , pp. 7126-7133.
International Search Report for PCT/US21/72319 dated Apr. 5, 2022.
Nogueira, Joao Carlos: "Forming Next-Generation Antibody Nanoparticle Conjugates through the Oriented Installation of Antibody Fragments"; University Collage London, (2019).
Maruani, A et al; "A Plug-and-Play Approach for the De Novo Generation of Dually Functionalised Bispecifics"; ChemRxiv; May 3, 2019.
Bahou, B., Richard, A. D., Maruani, A., Love, A. E., Javaid, F., Caddick, S., Barker, R. J., Chudasama, V. "Highly homogeneous antibody modification through optimisation of the synthesis and conjugation of functionalized dibromopyridazinediones" Organic & Biomolecular Chemistry, 2018, vol. 16, 1359.
Tsuchikama, K., An, Z. "Antibody-drug conjugates: recent advances in conjugation and linker chemistries" Protein Cell, 2018, vol. 9, 33-46.
Koprowski H, Steplewski Z, Mitchell K, Herlyn M, Herlyn D, Fuhrer P. Colorectal carcinoma antigens detected by hybridoma antibodies. Somatic Cell Genet. Nov. 1979;5(6):957-71.
Stern, Petr et al. "Comparison of Different Immunoassays for CA 19-9", Clinical Chemistry and Laboratory Medicine , vol. 39, No. 12, 2001, pp. 1278-1282.
La'ulu SL, Roberts WL (2007) Performance characteristics of five automated CA 19-9 assays. Am J Clin Pathol 127: 436-440.
Greene et al., Forming next-generation antibody—nanoparticle conjugates through the oriented installation of non-engineered antibody fragments, Chem. Sci., 9:79-87 (2018).
Robinson et al., Pyridazinediones deliver potent, stable, targeted and efficacious antibody—drug conjugates (ADCs) with a controlled loading of 4 drugs per antibod, RSC Adv., 7:9073-9077,(2017).
Maruani, A., Smith, M., Miranda, E. et al. A plug-and-play approach to antibody-based therapeutics via a chemoselective dual click strategy. Nat Commun 6, 6645 (2015).
Lee et al.,Enabling the controlled assembly of antibody conjugates with a loading of two modules without antibody engineering, Chem. Sci., 8:2056-2060v (2017).
Lee et al., Next-generation disulfide stapling: reduction and functional re-bridging all in one, Chem. Sci., 7:799-802, (2016).
Maruani et al., Site-selective multi-porphyrin attachment enables the formation of a next-generation antibody-based photodynamic therapeutic, Chem. Commun., 51:15304-15307 (2015).
Bryden et al., Assembly of High-Potency Photosensitizer—Antibody Conjugates through Application of Dendron Multiplier Technology, Bioconjugate Chem., 29:176-181, (2018).
Morgan et al., A novel synthetic chemistry approach to linkage-specific ubiquitin conjugation, Org. Biomol. Chem., 13:4165-4168, (2015).

CA19-9 MAb-TEG-TSPAE

CA19-9 MAb MCC-HEG-DMAE

DiBrPD-ZAE

DiBrPD-DMAE

DiBrPD-HEG-DMAE

DiBrPD-ISOZAE

DiBrPD-TEG-TSPAE

CA-19-9-MAb-DISFPD-HEG-DMAE

CA-19-9-MAb-DISFPD-TEG-TSPAE

DMAE-HEG-MCC

CA19-9 MAb MCC-HEG-DMAE

TSPAE-TEG-BAA, 10 eq.

CA19-9 MAb-TEG-TSPAE

BD 104613833-4

DiBrPD-ISOZAE

DiBrPD-ZAE

Standard Curves Generated Using DMAE-HEG Conjugates with Different Linker Chemistry

LABELS COMPRISING DIBROMOPYRIDAZINEDIONES FOR IMMUNOASSAYS AND METHODS OF PRODUCTION AND USE THEREOF

CROSS REFERENCE TO RELATED APPLICATIONS/INCORPORATION BY REFERENCE STATEMENT

This application is a 35 U.S.C. 371 national application of international application no. PCT/US2021/072319 filed 10 Nov. 2021, which claims priority of U.S. Provisional application No. 63/122,039 filed 7 Dec. 2020, the contents of which are fully incorporated herein by reference.

STATEMENT REGARDING FEDERALLY SPONSORED RESEARCH OR DEVELOPMENT

Not Applicable.

BACKGROUND

Pancreatic cancer accounts for about 3% of all cancers in the US and about 7% of all cancer deaths. Pancreatic cancer is difficult to diagnose early because of a lack of signs or symptoms. By the time symptoms begin to be observed, the tumors have often grown very large or have already spread outside the pancreas. As such, pancreatic cancer has one of the lowest survival rates of all cancers.

Tumor markers are useful in the diagnosis and management of various cancers. In particular (but not by way of limitation), cancer antigen 19-9 (CA 19-9) is a tumor marker for pancreatic and colorectal carcinoma. CA 19-9 is a glycoprotein, the sialylated form of the Lewis blood group antigen, and exists as a mucin in serum. CA 19-9 is synthesized by normal human pancreatic and biliary ductular cells and by gastric, colon, endometrial, and salivary epithelia, and elevated levels of CA 19-9 in serum can be an indication of pancreatic, gastric, and hepatobiliary malignancies. The original monoclonal antibody against CA 19-9 was developed from a human colon carcinoma cell line, as published in 1979 (Koprowski, et al. (1979) *Somatic Cell Genet.,* 5:957-971), and many different immunoassays for CA 19-9 have since been developed and are commercially available. The performance characteristics of these automated, commercially available CA 19-9 assays have also been assessed (see, for example (but not by way of limitation) Stern, et al. (2001) *Clin Chem Lab Med.,* 39:1278-1282; and La'ulu, et al. (2007) *Am J Clin Pathol,* 127:436-440). Non-limiting examples of the automated, commercially available CA 19-9 assays include the ADVIA® Centaur CA 19-9 assay (Siemens Healthcare Diagnostics Inc., Tarrytown, NY); the ARCHITECT® i2000 CA 19-$9_{XR}$ assay (Abbott Diagnostics, Abbott Park, IL); the IMMULITE® 2000 GI-MA assay (Diagnostic Products, Los Angeles, CA); the Elecsys E170 CA 19-9 assay (Roche Diagnostics, Indianapolis, IN); and the UniCel® Dxl 800 GI Monitor (Beckman Coulter, Fullerton, CA).

Despite the availability of automated, commercially available immunoassays, the sensitivity, accuracy, and ambient temperature effect (ATE) observed for these assays requires improvement.

Antibody-Drug-Conjugates (ADC) using functionalized dibromopyridazinediones have been reported in pharmaceutical research for therapeutic uses (see, for example, Bahou, et al. (2018) *Organic & Biomolecular Chemistry,* 16:1359-1366; Tsuchikama, et al. (2018) *Protein Cell,* 9:33-46; and US Patent Application Publication No. US 2015/0031861 (published Jan. 29, 2015)). It is suggested that, by holding the reduced intact antibody together in conjugation through new sulfhydryl chemistry, the binding affinity and long-term stability of these ADC could be better preserved for therapeutic uses. In particular, the DiBrPD linker platform has been employed in the generation of ADCs (Robinson et al. (2017) *RSC Adv.,* 7:9073-9077; Maruani, et al. (2015) *Nat. Commun.,* 6:6645), antibody conjugates (Lee et al. (2017) *Chem. Sci.,* 8:2056-2060; Lee et al. (2016) *Chem. Sci.,* 7:799-802), antibody-directed photosensitizers (Maruani et al. (2015) *Chem. Commun.,* 51:15304-15307; Bryden et al. (2018) *Bioconjugate Chem.,* 29:176-181), protein-protein conjugates (Morgan et al. (2015) *Org. Biomol. Chem.,* 13:4165-4168), and a targeted nanotherapeutic (Greene et al. (2018) *Chem. Sci.,* 9:79-87).

However, this antibody conjugation technique has not been explored in the diagnostic industry.

Thus, there is a need in the art for new and improved labels, linkers, and reagents for use in immunoassays that overcome the disadvantages and defects of the prior art. It is to such compositions, as well as kits and microfluidics devices containing same and methods of producing and using same, that the present disclosure is directed.

DETAILED DESCRIPTION

Figure 1:
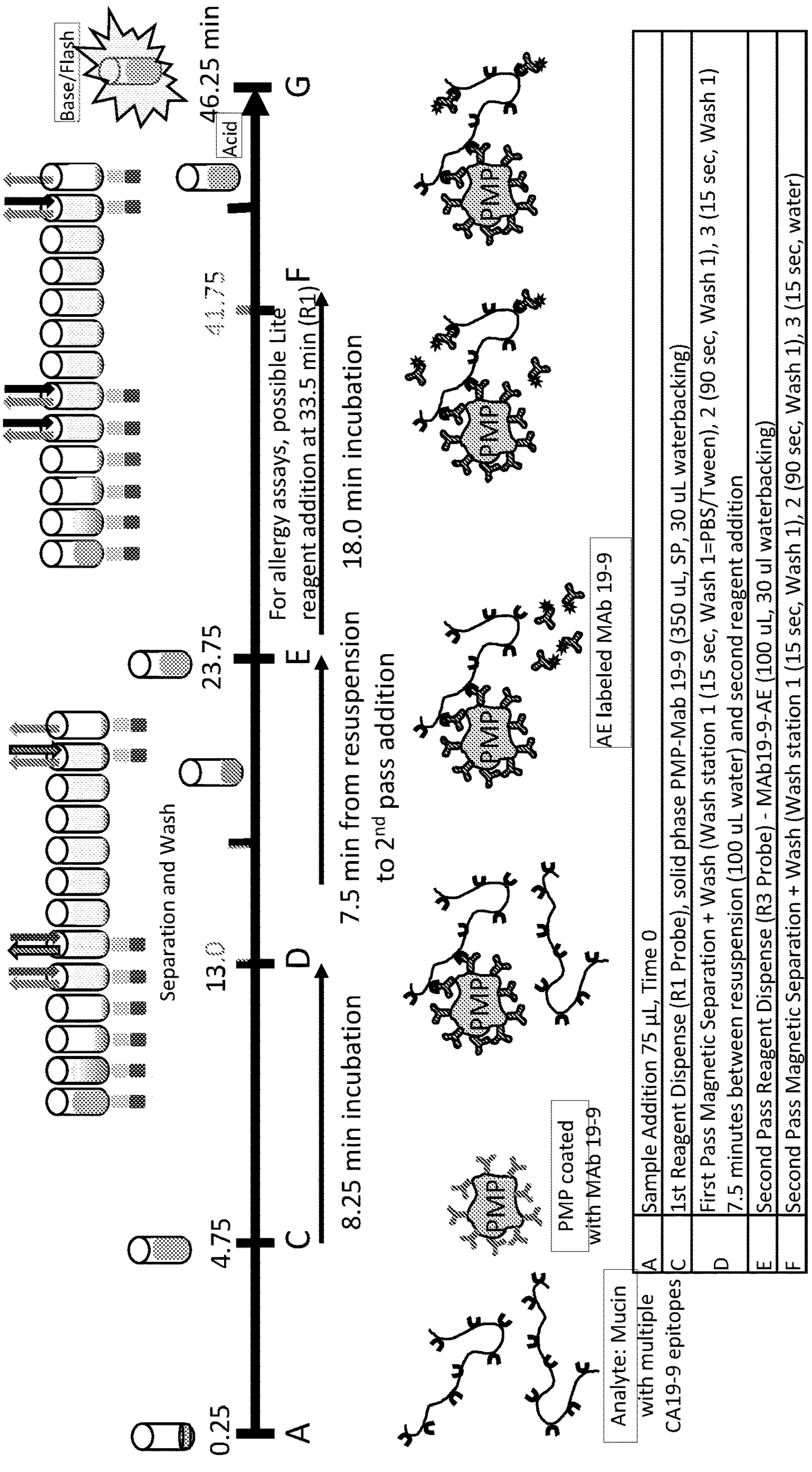
FIG. 1 schematically depicts one non-limiting embodiment of an assay format and principle for an immunoassay for the detection of the cancer marker CA 19-9 in accordance with the present disclosure. The immunoassay employs a solid phase reagent that includes paramagnetic particles (PMP) covalently labeled with a monoclonal anti-CA 19-9 antibody and a lite reagent that includes an anti-CA 19-9 monoclonal antibody-acridinium ester (CA 19-9-MAb-AE) conjugate.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutes and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term “a” or “an” when used in conjunction with the term “comprising” in the claims and/or the specification may mean “one,” but it is also consistent with the meaning of “one or more,” “at least one,” and “one or more than one.” As such, the terms “a,” “an,” and “the” include plural referents unless the context clearly indicates otherwise. Thus, for example, reference to “a compound” may refer to one or more compounds, two or more compounds, three or more compounds, four or more compounds, or greater numbers of compounds. The term “plurality” refers to “two or more.”

The use of the term “at least one” will be understood to include one as well as any quantity more than one, including but not limited to, 2, 3, 4, 5, 10, 15, 20, 30, 40, 50, 100, etc. The term “at least one” may extend up to 100 or 1000 or more, depending on the term to which it is attached; in addition, the quantities of 100/1000 are not to be considered limiting, as higher limits may also produce satisfactory results. In addition, the use of the term “at least one of X, Y, and Z” will be understood to include X alone, Y alone, and Z alone, as well as any combination of X, Y, and Z. The use of ordinal number terminology (i.e., “first,” “second,” “third,” “fourth,” etc.) is solely for the purpose of differentiating between two or more items and is not meant to imply any sequence or order or importance to one item over another or any order of addition, for example.

The use of the term “or” in the claims is used to mean an inclusive “and/or” unless explicitly indicated to refer to alternatives only or unless the alternatives are mutually exclusive. For example, a condition “A or B” is satisfied by any of the following: A is true (or present) and B is false (or not present), A is false (or not present) and B is true (or present), and both A and B are true (or present).

As used herein, any reference to “one embodiment,” “an embodiment,” “some embodiments,” “one example,” “for example,” or “an example” means that a particular element, feature, structure, or characteristic described in connection with the embodiment is included in at least one embodiment. The appearance of the phrase “in some embodiments” or “one example” in various places in the specification is not necessarily all referring to the same embodiment, for example. Further, all references to one or more embodiments or examples are to be construed as non-limiting to the claims.

Throughout this application, the term “about” is used to indicate that a value includes the inherent variation of error for a composition/apparatus/device, the method being employed to determine the value, or the variation that exists among the study subjects. For example, but not by way of limitation, when the term “about” is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words “comprising” (and any form of comprising, such as “comprise” and “comprises”), “having” (and any form of having, such as “have” and “has”), “including” (and any form of including, such as “includes” and “include”), or “containing” (and any form of containing, such as “contains” and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

The terms "analog" and "derivative" are used herein interchangeably and refer to a substance which comprises the same basic carbon skeleton and carbon functionality in its structure as a given compound, but can also contain one or more substitutions thereto. The term "substitution" as used herein will be understood to refer to the replacement of at least one substituent on a compound with a residue R. In certain non-limiting embodiments, R may include H, hydroxyl, thiol, a halide selected from fluoride, chloride, bromide, or iodide, a C1-C4 compound selected one of the following: linear, branched or cyclic alkyl, optionally substituted, and linear branched or cyclic alkenyl, wherein the optional substituents are selected from one or more alkenylalkyl, alkynylalkyl, cycloalkyl, cycloalkenylalkyl, arylalkyl, heteroarylalkyl, heterocyclealkyl, optionally substituted heterocycloalkenylalkyl, arylcycloalkyl, and arylheterocycloalkyl, each of which is optionally substituted wherein the optional substituents are selected from one or more of alkenylalkyl, alkynylalkyl, cycloalkyl, cycloalkenylalkyl, arylalkyl, alkylaryl, heteroarylalkyl, heterocyclealkyl, optionally substituted heterocycloalkenylalkyl, arylcycloalkyl, and arylheterocyclalkyl, phenyl, cyano, hydroxyl, alkyl, aryl, cycloalkyl, cyano, alkoxy, alkylthio, amino, —NH (alkyl), —NH(cycloalkyl)$_2$, carboxy, and —C(O))-alkyl.

The term "sample" as used herein will be understood to include any type of biological sample that may be utilized in accordance with the present disclosure. Examples of fluidic biological samples that may be utilized include, but are not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, combinations thereof, and the like.

The term "specific binding partner" or "analyte-specific binder" will be understood to refer to any molecule capable of specifically associating with a target analyte. For example but not by way of limitation, the binder/binding partner may be an antibody, a receptor, a ligand, aptamers, molecular imprinted polymers (i.e., inorganic matrices), any fragments thereof, and any combinations or derivatives thereof, as well as any other molecules capable of specific binding to the target analyte.

The term "antibody" is used in the broadest sense, and specifically (but not by way of limitation) covers monoclonal antibodies (including full length monoclonal antibodies), polyclonal antibodies, multispecific antibodies (e.g., bispecific antibodies), fragments of any of the above, and conjugates of any of the above, so long as they exhibit the desired biological activity of analyte binding. Thus, the term "antibody" or "antibody peptide(s)" refers to a full-length immunoglobulin molecule (i.e., an intact antibody) or an antigen-binding fragment thereof that competes with the intact antibody for specific antigen binding. Antigen-binding fragments may be produced by recombinant DNA techniques, or by enzymatic or chemical cleavage of intact antibodies. Antigen-binding fragments include Fab, Fab', F(ab')$_2$, Fv, scFv, disulfide linked Fv, Fd, diabodies, single-chain antibodies, single domain antibodies (such as but not limited to, NANOBODIES®, and other antibody fragments or conjugates thereof that retain at least a portion of the variable region of an intact antibody, antibody substitute proteins or peptides (i.e., engineered binding proteins/peptides), and combinations or derivatives thereof. See, e.g., Hudson et al. (Nature Med. (2003) 9:129-134). The antibody can be of any type or class (e.g., IgG, IgE, IgM, IgD, and IgA) or sub-class (e.g., IgG1, IgG2, IgG3, IgG4, IgA1, and IgA2).

The term "antigen binding fragment" or "antigen-binding portion" of an antibody, as used herein, refers to one or more fragments of an antibody that retain the ability to bind to an antigen. The antigen-binding function of an antibody can be performed by fragments of an intact antibody. Examples of binding fragments encompassed within the term "antigen-binding fragment" of an antibody include but are not limited to, Fab, Fab', F(ab')2, Fv, scFv, disulfide linked Fv, Fd, diabodies, single-chain antibodies, single domain antibodies (such as but not limited to, NANOBODIES®, isolated CDRH3, and other antibody fragments that retain at least a portion of the variable region of an intact antibody. These antibody fragments are obtained using conventional recombinant and/or enzymatic techniques and are screened for antigen binding in the same manner as intact antibodies.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes.

The terms "CDR," and its plural "CDRs," refer to a complementarity determining region (CDR) of an antibody or antibody fragment, which determine the binding character of an antibody or antibody fragment. In most instances, three CDRs are present in a light chain variable region (CDRL1, CDRL2 and CDRL3) and three CDRs are present in a heavy chain variable region (CDRH1, CDRH2 and CDRH3). CDRs contribute to the functional activity of an antibody molecule and are separated by amino acid sequences that comprise scaffolding or framework regions. Among the various CDRs, the CDR3 sequences, and particularly CDRH3, are the most diverse and therefore have the strongest contribution to antibody specificity. There are at least two techniques for determining CDRs: (1) an approach based on cross-species sequence variability (i.e., Kabat et al., Sequences of Proteins of Immunological Interest (National Institute of Health, Bethesda, Md. (1987), incorporated by reference in its entirety); and (2) an approach based on crystallographic studies of antigen-antibody complexes (Chothia et al., Nature, 342:877 (1989), incorporated by reference in its entirety).

The term "epitope" includes any protein determinant capable of specific binding to an immunoglobulin or T-cell receptor. In certain embodiments, an epitope is a region of an antigen that is specifically bound by an antibody. Epitopic determinants usually include chemically active surface groupings of molecules such as amino acids, sugar side chains, phosphoryl, or sulfonyl groups. In certain embodiments, an epitope may have specific three-dimensional structural characteristics (e.g., a "conformational epitope"), as well as specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope or closely related epitopes. In certain instances, for example, homologous proteins from different species may comprise the same epitope. In certain embodiments, an antibody specifically binds to an antigen with a dissociation constant of no greater than $10^{-6}$ M, $10^{-7}$ M, $10^{-8}$ M or $10^{-8}$ M. When an antibody specifically binds to a receptor or ligand (i.e., counterreceptor), it may substantially inhibit adhesion of the receptor to the ligand. As used herein, an antibody substantially inhibits adhesion of a receptor to a ligand when an excess of antibody reduces the quantity of receptor bound to ligand by at least about 20%, 40%, 60% or 80%, 85%, or 90% (as measured in an in vitro competitive binding assay).

An "isolated" antibody is one which has been separated and/or recovered from a component of the environment in which it was produced. Contaminant components of its production environment are materials which would interfere with diagnostic or therapeutic uses for the antibody, and may include enzymes, hormones, and other proteinaceous or non-proteinaceous solutes. In certain embodiments, the antibody will be purified as measurable by at least three different methods: 1) to greater than 50% by weight of antibody as determined by the Lowry method, such as more than 75% by weight, or more than 85% by weight, or more than 95% by weight, or more than 99% by weight; 2) to a degree sufficient to obtain at least 10 residues of N-terminal or internal amino acid sequence by use of a spiming cup sequentator, such as at least 15 residues of sequence; or 3) to homogeneity by SDS-PAGE under reducing or non-reducing conditions using Coomassie blue or, alternatively, silver stain. Isolated antibody includes the antibody in situ within recombinant cells since at least one component of the environment in which the antibody is produced will not be present. Ordinarily, however, isolated antibody will be prepared by at least one purification step. In addition, the "isolated antibody" is substantially free of other antibodies having different antigenic specificities. An isolated antibody may, however, have some cross-reactivity to other, related antigens.

The term "antibody mutant" refers to an amino acid sequence variant of an antibody wherein one or more of the amino acid residues have been modified. Such mutants necessarily have less than 100% sequence identity or similarity with the amino acid sequence having at least 75% amino acid sequence identity or similarity with the amino acid sequence of either the heavy or light chain variable domain of the antibody, such as at least 80%, or at least 85%, or at least 90%, or at least 95%.

The term "monoclonal antibody" as used herein refers to an antibody obtained from a population of substantially homogeneous antibodies that specifically bind to the same epitope, i.e., the individual antibodies comprising the population are identical except for possible naturally occurring mutations that may be present in minor amounts. In contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that in one method of production they may be synthesized by a hybridoma culture, and thus are uncontaminated by other immunoglobulins. The modifier "monoclonal" indicates the character of the antibody as being obtained from a substantially homogeneous population of antibodies, and is not to be construed as requiring production of the antibody by any particular method. For example, in one embodiment, the monoclonal antibodies produced in accordance with the present disclosure may be made by the hybridoma method first described by Kohler and Milstein (Nature, 256:495 (1975)).

The monoclonal antibodies utilized in accordance with the present disclosure may be produced by any methodology known in the art including, but not limited to, a result of a deliberate immunization protocol; a result of an immune response that results in the production of antibodies naturally in the course of a disease or cancer; phage-derived antibodies; and the like. In addition to the hybridoma production method listed above, the monoclonal antibodies of the present disclosure may be produced by other various methods such as, but not limited to, recombinant DNA methods (see, e.g., U.S. Pat. No. 4,816,567); isolation of antibody fragments from a phage display library (see, e.g., Clackson et al., Nature (1991) 352:624-628; and Marks et al., J. Mol. Biol. (1991) 222:581-597); as well as various other monoclonal antibody production techniques (see, e.g., Harlow and Lane (1988) Antibodies: A Laboratory Manual (Cold Spring Harbor Laboratory, Cold Spring Harbor, N.Y.)). Further, many monoclonal antibodies that may be utilized in the conjugates and methods disclosed or otherwise contemplated herein are widely commercially available, and therefore no further description thereof is deemed necessary.

As used herein, "substantially pure" means an object species is the predominant species present (i.e., on a molar basis it is more abundant than any other individual species in the composition). Generally, a substantially pure composition will comprise more than about 50% percent of all macromolecular species present in the composition, such as more than about 55%, 60%, 65%, 70%, 75%, 80%, 85%, 90%, 95%, and 99%. In one embodiment, the object species is purified to essential homogeneity (contaminant species cannot be detected in the composition by conventional detection methods) wherein the composition consists essentially of a single macromolecular species.

An "analyte" is a molecule that is capable of being recognized by an analyte-specific binding partner, such as (but not limited to) an antibody. An analyte comprises at least one antigenic determinant or "epitope," which is the region of the analyte which binds to the analyte-specific binding partner (i.e., antibody).

The term "LOCI®" as used herein refers to a commercially used immunoassay technique based on Luminescent Oxygen Channeling Assay (LOCI®) technology. The LOCI® advanced chemiluminescence assay is described, for example, in U.S. Pat. No. 5,340,716 (Ullman et al.), the entire contents of which are expressly incorporated herein by reference. The currently available LOCI® technology has high sensitivity and uses several reagents. In particular, the LOCI® assay requires that two of these reagents (referred to as a "sensibead" and a "chemibead") be held by other specific binding partner assay reagents in a manner whereby the sensibead and chemibead are in close proximity to one another to achieve a signal. Upon exposure to light at a certain wavelength, the sensibead releases singlet oxygen, and if the two beads are in close proximity, the singlet oxygen is transferred to the chemibead; this causes a chemical reaction that results in the chemibead giving off light that can be measured at a different wavelength.

For example (but not by way of limitation), an assay similar to a LOCI assay may include (i) a composition comprising: a singlet oxygen-activatable chemiluminescent compound and a fluorescent molecule that is excited by the activated chemiluminescent compound; and (ii) a composition comprising a sensitizer capable of generating singlet oxygen in its excited state.

Certain non-limiting embodiments of the present disclosure are directed to a label that can be utilized with an analyte-specific binder, such as (but not limited to) an analyte-binding protein or peptide (such as, but not limited to, an antibody or fragment thereof). In certain non-limiting embodiments, the label includes a dibromopyridazinedione (DiBrPD) and a signal molecule (A) linked via a spacer (B) and having the structure of Formula I:

Formula I

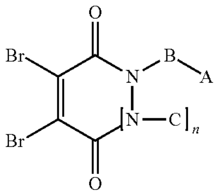

n = 1 or 0 wherein: "A" comprises a signal molecule selected from a luminescent label, and an enzymatic label; "B" is a spacer selected from an alkyl, alkenyl, alkynyl, or aralkyl group (which can be linear or branched), wherein the spacer contains 0 to 20 heteroatoms; and when n=1, "C" is a group comprising 1 to 40 carbon atoms and 0 to 20 heteroatoms.

For example, but not by way of limitation, the label may have the structure of Formula II or III:

Formula II

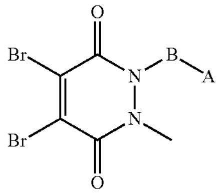

or

Formula III

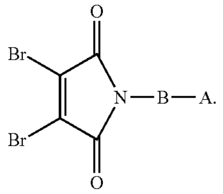

Any luminescent labels known in the art or otherwise contemplated herein may be utilized in accordance with the present disclosure. Non-limiting examples of particular types of luminescent labels that may be utilized include chemiluminescent labels, fluorescent labels, luminescent oxygen channeling beads or similar compositions, electrochemiluminescence (ECL) labels, and the like, as well as any combinations thereof.

Any chemiluminescent labels known in the art or otherwise contemplated herein may be utilized as the signal molecule of "A" in Formula I. Many different chemiluminescent labels are known in the art and available commercially; further, it is well within the skill of a person of ordinary skill in the art to select a particular chemiluminescent label for use in accordance with the present disclosure.

In particular non-limiting embodiments, the chemiluminescent label utilized in accordance with the present disclosure has the structure of Formula IV:

Formula IV

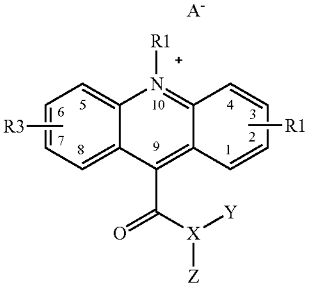

wherein "R1" is selected from the group consisting of an alkyl, alkenyl, alkynyl, or aralkyl group of 1 to 35 carbon atoms and 0 to 20 heteroatoms; a sulfopropyl or sulfobutyl group; and a group —$R^a$—Z, where $R^a$ is a divalent radical selected from alkyl, alkenyl, alkynyl, aryl, or aralkyl group of 1 to 35 carbon atoms and 0 to 20 heteroatoms. In addition, "R2" is placed at one or more of positions C1 to C4, and each "R2" is independently selected from the group consisting of hydrogen, alkyl, OR, OH, SR, SH, $NH_2$, and NR'R", wherein R, R', and R" are each independently selected from the group consisting of an alkyl, alkenyl, alkynyl, aryl, and aralkyl group, wherein each group contains 0 to 20 heteroatoms. Also, "R3" is placed at one or more of positions C5 to C8, and each "R3" is independently selected from the group consisting of hydrogen, alkyl, OR, OH, SR, SH, $NH_2$, and NR'R", wherein R, R', and R" are each independently selected from the group consisting of an alkyl, alkenyl, alkynyl, aryl, and aralkyl group, wherein each group contains 0 to 20 heteroatoms. Further, "X" is oxygen or nitrogen, and "Z" is omitted when "X" is oxygen and is $SO_2$—Y when "X" is nitrogen. Also, "Y" is a group selected from a halogenated or unhalogenated, branched or straight-chained alkyl group; a substituted or unsubstituted aryl group; and a heterocyclic ring group. The "Y" group also comprises 0 to 20 heteroatoms, and further comprises a functional group that links to the spacer "B" of Formula I. In addition, "$A^-$" is a counter ion introduced, for example (but not by way of limitation) to pair with the quaternary nitrogen of said acridinium nucleus, and "$A^-$" is selected from the group consisting of $CH_3SO_4^-$, $FSO_3^-$, $CF_3SO_4^-$, $C_4F_9SO_4^-$, $CH_3C_6H_4SO_3^-$, a halide, $CF_3COO^-$, $CH_3COO^-$, and $NO_3^-$.

In particular non-limiting embodiments, the chemiluminescent label utilized in accordance with the present disclosure is a chemiluminescent acridinium ester having the structure of Formula V:

Formula V

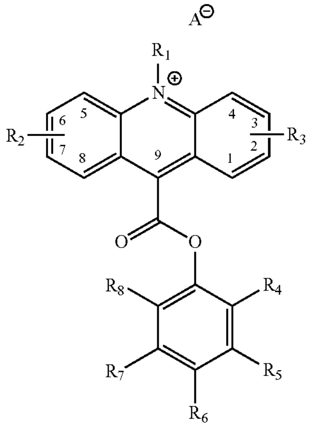

wherein: "$R_1$," "$R_2$," "$R_3$," and "$A^-$" are as defined above in reference to Formula IV; each of "$R_4$" and "$R_8$" is independently selected from hydrogen or an alkyl, alkenyl, alkynyl, alkoxyl (—OR), alkylthiol (—SR), or substituted amino group that serve, for example (but not by way of limitation) to stabilize the —COX— linkage between the acridinium nucleus and the "Y" moiety through steric and/or electronic effect. In addition, each of "$R_5$," "$R_6$," and "$R_7$" is independently selected from hydrogen or an alkyl, alkenyl, alkynyl, aryl, or aralkyl group, wherein each group contains 0 to 20 heteroatoms. Also, one of "$R_5$," "$R_6$," and "$R_7$" further comprises a functional group that links to the spacer "B" of Formula I. Functional groups that may be utilized in accordance with the present disclosure include, but are not limited to, the following groups:

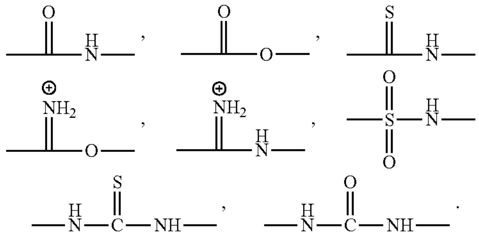

In particular non-limiting embodiments, the chemiluminescent label utilized in accordance with the present disclosure is a dimethylphenyl acridinium ester having the structure of Formula VI:

Formula VI

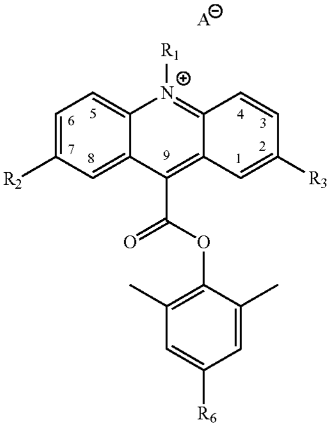

wherein "$R_1$" is a methyl or a sulfopropyl group; each of "$R_2$" and "$R_3$" is independently selected from hydrogen or a methoxy, sulfopropyloxyl, or poly(ethylene)glycoloxy group; and "$R_6$" is an amide group (CONH—) connecting to the spacer "B" of Formula I. "$A^-$" is as defined in Formula IV.

Any fluorescent labels known in the art or otherwise contemplated herein may be utilized as the signal molecule of "A" in Formula I. Many different fluorescent labels are known in the art and available commercially; further, it is well within the skill of a person of ordinary skill in the art to select a particular fluorescent label for use in accordance with the present disclosure. Non-limiting examples of fluorescent labels that may be utilized include xanthene derivatives such as (but not limited to) fluorescein, rhodamine, Oregon green, eosin, and Texas red; dipyrromethene derivatives such as (but not limited to) BODIPY and aza-BODIPY; cyanine derivatives such as (but not limited to) cyanine, indocarbocyanine, oxacarbocyanine, thiacarbocyanine, and merocyanine; squaraine derivatives and ring-substituted squaraines such as (but not limited to) Seta and Square dyes; squaraine rotaxane derivatives; naphthalene derivatives such as (but not limited to) dansyl and prodan derivatives; coumarin derivatives; oxadiazole derivatives such as (but not limited to) pyridyloxazole, nitrobenzoxadiazole, and benzoxadiazole; anthracene derivatives such as (but not limited to) anthraquinones, including DRAQ5, DRAQ7, and CyTRAK Orange; pyrene derivatives such as (but not limited to) cascade blue; oxazine derivatives such as (but not limited to) Nile red, Nile blue, cresyl violet, and oxazine 170; acridine derivatives such as (but not limited to) proflavin, acridine orange and acridine yellow; arylmethine derivatives such as (but not limited to) auramine, crystal violet, and malachite green; tetrapyrrole derivatives such as (but not limited to) porphin, phthalocyanine, and bilirubin.

Any luminescent oxygen channeling beads or similar compositions known in the art or otherwise contemplated herein may be utilized in accordance with the present disclosure. Non-limiting examples thereof include (i) a composition comprising a singlet oxygen-activatable chemiluminescent and a fluorescent molecule that is excited by the activated chemiluminescent compound; and (ii) a composition comprising a sensitizer capable of generating singlet oxygen in its excited state. Particular non-limiting examples thereof include a LOCI chemibead containing thioxene and europium dye.

Any electrochemiluminescence (ECL) labels known in the art or otherwise contemplated herein may be utilized in accordance with the present disclosure. Many different ECL labels are known in the art and available commercially;

further, it is well within the skill of a person of ordinary skill in the art to select a particular ECL label for use in accordance with the present disclosure. One non-limiting example thereof is a ruthenium-complex.

Any enzymatic labels known in the art or otherwise contemplated herein may be utilized in accordance with the present disclosure. Many different enzymatic labels are known in the art and available commercially; further, it is well within the skill of a person of ordinary skill in the art to select a particular enzymatic label for use in accordance with the present disclosure. Non-limiting examples of enzymatic labels that may be utilized include horseradish peroxidase (HRP), alkaline phosphatase (ALP); β-galactosidase (β-Gal), glucose oxidase (GO) and the like, as well as any combinations thereof.

In a particular non-limiting embodiment, the label is a dibromopyridazinedione-dimethylphenyl acridinium ester (DiBrPD-DMAE) having the structure of Formula VII:

Formula VII

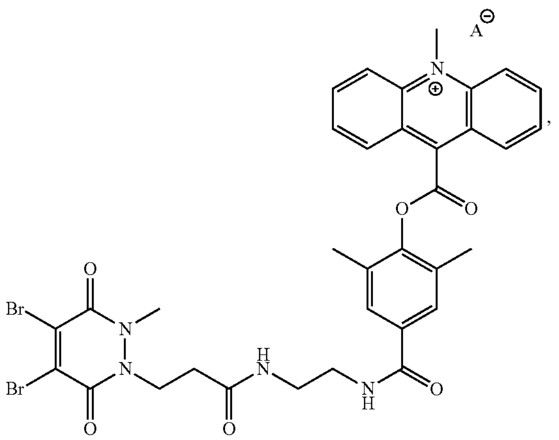

wherein "$A^-$" is as defined in Formula IV.

In a particular non-limiting embodiment, the label is a dibromopyridazinedione-hexa(ethylene)glycol-dimethylphenyl acridinium ester (DiBrPD-HEGAE) having the structure of Formula VIII:

Formula VIII

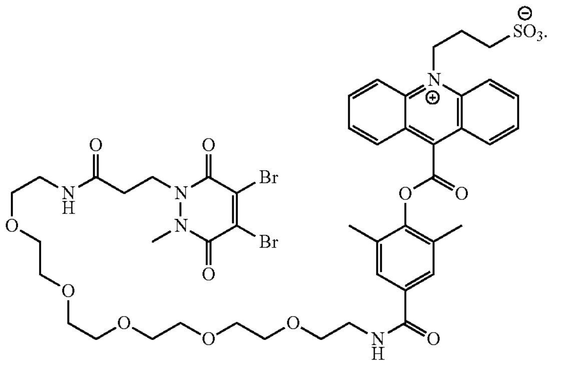

In a particular non-limiting embodiment, the label is a dibromopyridazinedione-zwitterionic acrinidium ester (DiBrPD-ZAE) having the structure of Formula IX:

Formula IX

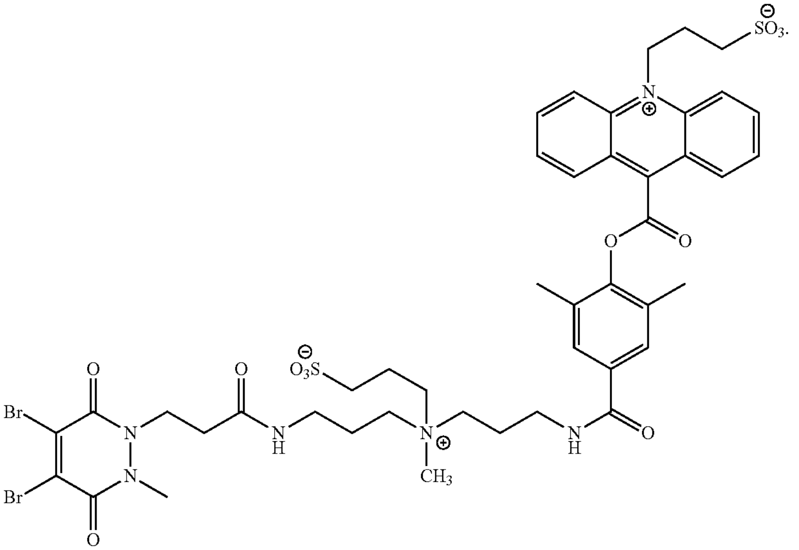

In a particular non-limiting embodiment, the label is a dibromopyridazinedione-triethylene glycol-tri-sulfo propyl acridinium ester (DiBrPD-TEG-TSPAE) having the structure of Formula X:

Formula X

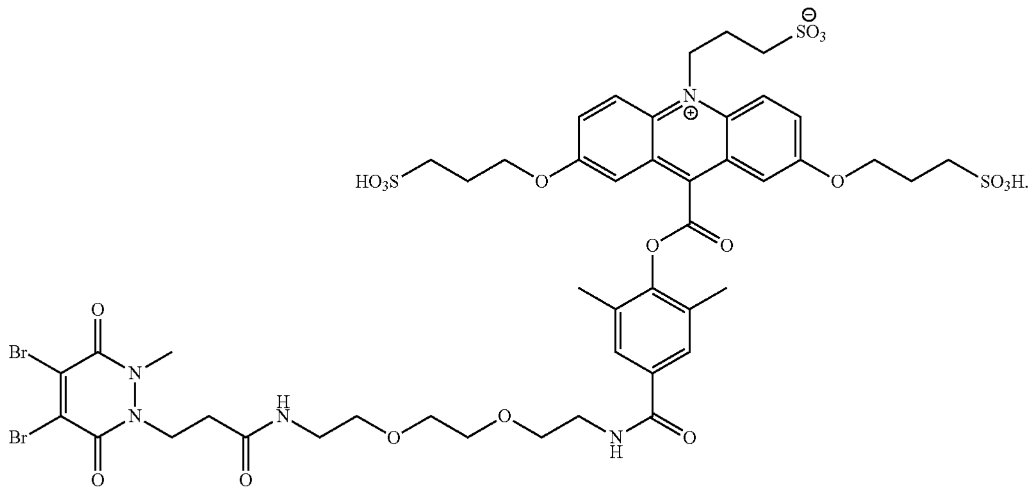

In a particular non-limiting embodiment, the label is a dibromopyridazinedione-2-isopropyl acridinium ester (DiBrPD-ISOZAE) having the structure of Formula XI:

Formula XI

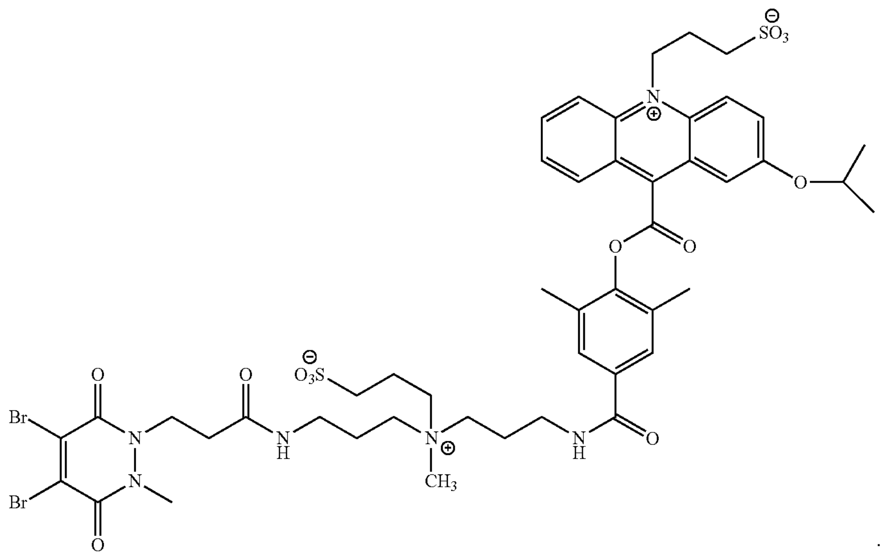

Certain non-limiting embodiments of the present disclosure are directed to a conjugate that comprises one or more of any of the labels described or otherwise contemplated herein above. For example (but not by way of limitation), the conjugate can include an analyte-specific binder having at least one disulfide bond capable of reduction to two sulfhydryl groups, and at least one of any of these labels directly or indirectly attached to the two sulfhydryl groups of the analyte-specific binder, thereby forming the conjugate.

In certain particular (but non-limiting) embodiments, the conjugate has the structure of Formula XII:

Formula XII

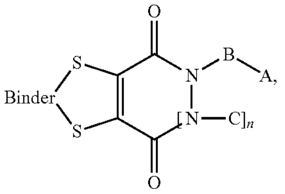

n = 1 or 0 wherein "Binder" represents the analyte-specific binder, and "A," "B," and "C" are as defined in Formula I. In particular (but non-limiting) embodiments, "A" is defined as having the structure of one of Formulas IV, V, or VI.

For example (but not by way of limitation), the conjugate may have the structure of Formula XIII or XIV:

Formula XIII

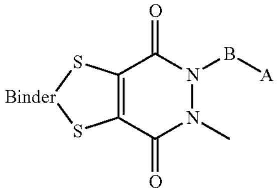

or

Formula XIV

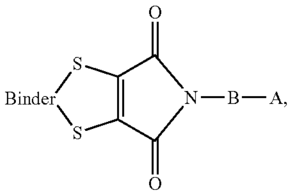

wherein "Binder" represents the analyte-specific binder, and "A," "B," and "C" are as defined in Formula I.

The analyte-specific binder may be any protein or peptide known in the art or otherwise contemplated herein, so long as the protein/peptide has at least one disulfide bond capable of reduction to two sulfhydryl groups and can be conjugated to a label to function in accordance with the present disclosure. In certain non-limiting embodiments, the analyte-specific binder has at least two, at least three, or at least four disulfide bonds (or more), each capable of being reduced to two sulfhydryl groups for attachment to the label.

The analyte-specific binder may bind to any target analyte for which detection is desired. In certain non-limiting embodiments, the target analyte may be a cancer marker or a cardiac marker. Non-limiting examples of cancer markers include CA 19-9, CA 125, CA 15-3, prostate-specific antigen (PSA), carcinoembryonic antigen (CEA), alpha-fetoprotein (AFP), human chorionic gonadotropin (hCG), and the like. Non-limiting examples of cardiac markers include troponin (TnI), BNP (B-type natriuretic peptide), proBNP (pro B-type natriuretic peptide; such as, but not limited to, N-terminal pro B-type natriuretic peptide (NT-proBNP)), creatinine kinase (CK-MB), lactate dehydrogenase (LDH), and the like.

In certain particular (but non-limiting) embodiments, the analyte-specific binder is selected from the group consisting of a monoclonal antibody or fragment thereof, a polyclonal antibody or fragment thereof, an analyte-binding protein or fragment thereof, a peptide, and combinations or derivatives thereof.

In certain particular (but non-limiting) embodiments, the analyte-specific binder is a monoclonal antibody or fragment thereof. The hinge region of the monoclonal antibody or fragment thereof includes four inter-chain disulfide bonds in the hinge region thereof, and each of the four inter-chain disulfide bonds can be reduced to two sulfhydryl groups for attachment to any of the labels of the present disclosure. As such, conjugates containing monoclonal antibodies (or fragments thereof) as the protein can include up to four labels molecules therein.

As attachment of the label is occurring in the non-variable, hinge region of the monoclonal antibody, the antibody specificity of the monoclonal antibody is completely irrelevant; the ability of any monoclonal antibody (or fragment thereof) to bind to the label is independent of antibody specificity. Therefore, any monoclonal antibody (or fragment thereof) can be utilized in accordance with the present disclosure, and as such, no further description of the characteristics or structures of the antibodies (or fragments thereof) that can be used in accordance with the present disclosure is deemed necessary.

In one particular (but non-limiting) embodiment, the monoclonal antibody or fragment thereof is an anti-CA 19-9 monoclonal antibody or fragment thereof. Anti-CA 19-9 monoclonal antibodies are well known in the art and widely available commercially; for example (but not by way of limitation), anti-CA 19-9 monoclonal antibodies that can be utilized in accordance with the present disclosure can be obtained from Abcam (Cambridge, UK); Abnova Corporation (Walnut, CA); Agilent Technologies (Santa Clara, CA); Antibodies-Online Inc. (Limerick, PA); Biocare Medical (Pacheco, CA); Biorbyt Ltd. (St. Louis, MO); Creative Diagnostics (Shirley, NY); Cell Sciences (Newburyport, MA); EastCoast Bio (North Berwick, ME); Enzo Life Sciences, Inc. (Farmingdale, NY); Fitzgerald Industries International (Acton, MA); LifeSpan BioSciences (Seattle, WA); MyBioSource, Inc. (San Diego, CA); OriGene Technologies, Inc. (Rockville, MD); RayBiotech Life (Peachtree Corners, GA); Sigma Aldrich (St. Louis, MO); Thermo Fisher Scientific (Waltham, MA); US Biological Life Sciences (Salem, MA); and many others.

In one particular (but non-limiting) embodiment, the analyte-specific binder is an anti-CA125 monoclonal antibody or fragment thereof. Anti-CA125 monoclonal antibodies are well known in the art and widely available commercially; for example (but not by way of limitation), anti-CA125 monoclonal antibodies that can be utilized in accordance with the present disclosure can be obtained from Agilent Technologies (Santa Clara, CA); Anogen (Mississauga, ON); Biocare Medical (Pacheco, CA); Biorbyt Ltd. (St. Louis, MO); Creative Diagnostics (Shirley, NY); Enzo Life Sciences, Inc. (Farmingdale, NY); HyTest Ltd. (Turku, Finland); MyBioSource, Inc. (San Diego, CA); Progen (Wayne, PA); QED Bioscience Inc. (San Diego, CA); ProSci, Inc. (Poway, CA); RayBiotech Life (Peachtree Corners, GA); US Biological Life Sciences (Salem, MA); and many others.

In another particular (but non-limiting) embodiment, the analyte-specific binder is an anti-CA-15-3 monoclonal antibody or fragment thereof. Anti-CA-15-3 monoclonal antibodies are well known in the art and widely available commercially; for example (but not by way of limitation), anti-CA-15-3 monoclonal antibodies that can be utilized in accordance with the present disclosure can be obtained from Abeomics (San Diego, CA); Biorbyt Ltd. (St. Louis, MO); Cell Sciences (Newburyport, MA); Creative Diagnostics (Shirley, NY); LifeSpan BioSciences (Seattle, WA); MyBioSource, Inc. (San Diego, CA); Novus Biologicals (Centennial, CO); OriGene Technologies, Inc. (Rockville, MD); US Biological Life Sciences (Salem, MA); and many others.

In another particular (but non-limiting) embodiment, the analyte-specific binder is an anti-Prostate-specific antigen (anti-PSA) monoclonal antibody or fragment thereof. Anti-PSA monoclonal antibodies are well known in the art and widely available commercially; for example (but not by way of limitation), anti-PSA monoclonal antibodies that can be utilized in accordance with the present disclosure can be obtained from Abeomics (San Diego, CA); Anogen (Mississauga, ON); Biorbyt Ltd. (St. Louis, MO); Bioss Inc. (Boston, MA); G-Biosciences (St. Louis, MO); Huabio (Boston, MA); MyBioSource, Inc. (San Diego, CA); NSJ Bioreagents (San Diego, CA); OriGene Technologies, Inc. (Rockville, MD); RayBiotech Life (Peachtree Corners, GA); US Biological Life Sciences (Salem, MA); and many others.

In another particular (but non-limiting) embodiment, the analyte-specific binder is an anti-Carcinoembryonic antigen (anti-CEA) monoclonal antibody or fragment thereof. Anti-CEA monoclonal antibodies are well known in the art and widely available commercially; for example (but not by way of limitation), anti-CEA monoclonal antibodies that can be utilized in accordance with the present disclosure can be obtained from Abcam (Cambridge, UK); Abeomics (San Diego, CA); Biorbyt Ltd. (St. Louis, MO); BioVision Inc. (Milpitas, CA); G-Biosciences (St. Louis, MO); Huabio (Boston, MA); LifeSpan BioSciences (Seattle, WA); MyBioSource, Inc. (San Diego, CA); NSJ Bioreagents (San Diego, CA); RayBiotech Life (Peachtree Corners, GA); Thermo Fisher Scientific (Waltham, MA); and many others.

In another particular (but non-limiting) embodiment, the analyte-specific binder is an anti-human chorionic gonadotropin (anti-hCG) monoclonal antibody or fragment thereof. Anti-hCG monoclonal antibodies are well known in the art and widely available commercially; for example (but not by way of limitation), anti-hCG monoclonal antibodies that can be utilized in accordance with the present disclosure can be obtained from Anogen (Mississauga, ON); Biorbyt Ltd. (St. Louis, MO); Bioss Inc. (Boston, MA); BioVision Inc. (Milpitas, CA); Creative Diagnostics (Shirley, NY); EastCoast Bio (North Berwick, ME); MyBioSource, Inc. (San Diego, CA); OriGene Technologies, Inc. (Rockville, MD); RayBiotech Life (Peachtree Corners, GA); US Biological Life Sciences (Salem, MA); and many others.

In another particular (but non-limiting) embodiment, the analyte-specific binder is an anti-troponin (anti-TnI) monoclonal antibody or fragment thereof. Anti-TnI monoclonal antibodies are well known in the art and widely available commercially; for example (but not by way of limitation), anti-TnI monoclonal antibodies that can be utilized in accordance with the present disclosure can be obtained from Bio-Rad (Hercules, CA); Biorbyt Ltd. (St. Louis, MO); Bioss Inc. (Boston, MA); LifeSpan BioSciences (Seattle, WA); MyBioSource, Inc. (San Diego, CA); Novus Biologicals (Centennial, CO); QED Bioscience Inc. (San Diego, CA); RayBiotech Life (Peachtree Corners, GA); Santa Cruz Biotechnology, Inc. (Dallas, TX); Thermo Fisher Scientific (Waltham, MA); and many others.

In another particular (but non-limiting) embodiment, the analyte-specific binder is an anti-B-type natriuretic peptide (anti-BNP) monoclonal antibody or fragment thereof. Anti-BNP monoclonal antibodies are well known in the art and widely available commercially; for example (but not by way of limitation), anti-BNP monoclonal antibodies that can be utilized in accordance with the present disclosure can be obtained from Abcam (Cambridge, UK); Bio-Rad (Hercules, CA); Biorbyt Ltd. (St. Louis, MO); Bioss Inc. (Boston, MA); HyTest Ltd. (Turku, Finland); LifeSpan BioSciences (Seattle, WA); MyBioSource, Inc. (San Diego, CA); Novus Biologicals (Centennial, CO); Thermo Fisher Scientific (Waltham, MA); US Biological Life Sciences (Salem, MA); and many others.

In another particular (but non-limiting) embodiment, the analyte-specific binder is an anti-proBNP monoclonal antibody or fragment thereof. Anti-proBNP monoclonal antibodies are well known in the art and widely available commercially; for example (but not by way of limitation), anti-proBNP monoclonal antibodies that can be utilized in accordance with the present disclosure can be obtained from Biorbyt Ltd. (St. Louis, MO); US Biological Life Sciences (Salem, MA); and many others.

In another particular (but non-limiting) embodiment, the analyte-specific binder is an anti-creatinine kinase-MB (anti-CK-MB) monoclonal antibody or fragment thereof. Anti-CK-MB monoclonal antibodies are well known in the art and widely available commercially; for example (but not by way of limitation), anti-CK-MB monoclonal antibodies that can be utilized in accordance with the present disclosure can be obtained from Abcam (Cambridge, UK); Bio-Rad (Hercules, CA); Biorbyt Ltd. (St. Louis, MO); Bioss Inc. (Boston, MA); LifeSpan BioSciences (Seattle, WA); MyBioSource, Inc. (San Diego, CA); Novus Biologicals (Centennial, CO); RayBiotech Life (Peachtree Corners, GA); Santa Cruz Biotechnology, Inc. (Dallas, TX); Thermo Fisher Scientific (Waltham, MA); US Biological Life Sciences (Salem, MA); and many others.

In another particular (but non-limiting) embodiment, the analyte-specific binder is an anti-lactate dehydrogenase (anti-LDH) monoclonal antibody or fragment thereof. Anti-LDH monoclonal antibodies are well known in the art and widely available commercially; for example (but not by way of limitation), anti-LDH monoclonal antibodies that can be utilized in accordance with the present disclosure can be obtained from Abcam (Cambridge, UK); LifeSpan BioSciences (Seattle, WA); Millipore Sigma (St. Louis, MO); MyBioSource, Inc. (San Diego, CA); OriGene Technologies, Inc. (Rockville, MD); Santa Cruz Biotechnology, Inc. (Dallas, TX); Thermo Fisher Scientific (Waltham, MA); US Biological Life Sciences (Salem, MA); and many others.

In other particular (but non-limiting) embodiments, the analyte-specific binder is a non-antibody protein or peptide. Non-antibody analyte binders are well known in the art and have been studied extensively, and thus no further description thereof is deemed necessary. Particular non-limiting examples thereof that can be utilized in accordance with the present disclosure include folate binding protein (FBP), FK-506 binding protein (FKBP), VB12 intrinsic factor, and the like, as well as any fragments thereof.

When the analyte-specific binder has at least two, at least three, or at least four disulfide bonds (or more), each capable of being reduced to two sulfhydryl groups for attachment to the label, then the conjugate may include a label for each disulfide bond present in the binder. For example (but not by way of limitation), the conjugate may include at least one, at least two, at least three, at least four, or more labels directly or indirectly attached to the analyte-specific binder. In a particular (but non-limiting) example, an antibody has four inter-chain disulfide bonds in the hinge region thereof, and thus one, two, three, or four labels can bind to each monoclonal antibody. When two or more labels are present in the conjugate, the labels may be the same and/or different.

Certain non-limiting embodiments of the present disclosure are directed to an immunoassay kit that contains one or more of any of the labels and/or conjugates disclosed or otherwise contemplated herein. The selection of the label(s) and/or conjugate(s) will depend on the particular assay format to be utilized, and such selection is well within the purview of a person having ordinary skill in the art.

In certain particular (but non-limiting) embodiments, the immunoassay kit includes a first reagent comprising any of the conjugates described herein above or otherwise contemplated herein (and containing a first analyte-specific binder having at least one label attached thereto); and a second reagent comprising a solid phase having a second analyte-specific binder directly or indirectly attached thereto (where the second analyte-specific binder may be any of the analyte-specific binders disclosed or otherwise contemplated herein). Each of the first and second analyte-specific binders of the first and second reagents specifically binds to an epitope of the target analyte to be detected. In a particular (but non-limiting) embodiment, the epitopes of the target analyte to which the first and second analyte-specific binders bind do not substantially overlap, such that the first and second analyte-specific binders can bind simultaneously to the same target analyte molecule.

Any monoclonal antibodies or fragments thereof may be utilized as the first and second analyte-specific binders of the first and second reagents, so long as both antibodies can simultaneously bind to the same target analyte molecule.

In certain non-limiting embodiments of the present disclosure, each of the monoclonal antibodies or fragments thereof of the first and second reagents is an anti-CA 19-9 monoclonal antibody or fragment thereof. Anti-CA 19-9 monoclonal antibodies/fragments thereof are known in the art and commercially available; see, for example (but not by way of limitation), the anti-CA 19-9 MAb (Catalog NO: 210-580; clone 1116NS19-9) from Fujirebio Diagnostics Inc. (Malvern, PA), or any of the other anti-CA 19-9 monoclonal antibodies/fragments disclosed herein above.

The assay reagents present in the kits may be provided in any form that allows them to function in accordance with the present disclosure. For example, but not by way of limitation, each of the reagents may be provided in liquid form and disposed in bulk and/or single aliquot form within the kit. Alternatively, in a particular (but non-limiting) embodiment, one or more of the reagents may be disposed in the kit in the form of a single aliquot lyophilized reagent. The use of dried reagents in microfluidics devices is described in detail in U.S. Pat. No. 9,244,085 (Samproni), the entire contents of which are hereby expressly incorporated herein by reference.

In addition to the assay reagents described in detail herein above, the kits may further contain other reagent(s) for conducting any of the particular assays described or otherwise contemplated herein. The nature of these additional reagent(s) will depend upon the particular assay format, and identification thereof is well within the skill of one of ordinary skill in the art; therefore, no further description thereof is deemed necessary. Also, the components/reagents present in the kits may each be in separate containers/compartments, or various components/reagents can be combined in one or more containers/compartments, depending on the cross-reactivity and stability of the components/reagents. In addition, the kit may include a microfluidics device in which the components/reagents are disposed.

The relative amounts of the various components/reagents in the kits can vary widely to provide for concentrations of the components/reagents that substantially optimize the reactions that need to occur during the assay methods and further to optimize substantially the sensitivity of an assay. Under appropriate circumstances, one or more of the components/reagents in the kit can be provided as a dry powder, such as a lyophilized powder, and the kit may further include excipient(s) for dissolution of the dried reagents; in this manner, a reagent solution having the appropriate concentrations for performing a method or assay in accordance with the present disclosure can be obtained from these components. Non-limiting examples of other reagents that can be included in the kits include wash solutions, dilution solutions, excipients, interference solutions, positive controls, negative controls, calibration reagents, quality control reagents, and the like. In addition, the kit can further include a set of written instructions explaining how to use the kit. A kit of this nature can be used in any of the methods described or otherwise contemplated herein.

Certain non-limiting embodiments of the present disclosure are directed to a method of producing any of the conjugates disclosed or otherwise contemplated herein. The method includes incubating an analyte-specific binder having at least one disulfide bond with at least one of any of the labels described or otherwise contemplated herein under conditions which reduce each disulfide bond of the analyte-specific binder to two sulfhydryl groups and directly or indirectly conjugate the at least one label to the two sulfhydryl groups of the analyte-specific binder and thereby produce the conjugate.

In certain particular (but non-limiting) embodiments, the analyte-specific binder is selected from the group consisting of a monoclonal antibody or fragment thereof, a polyclonal antibody or fragment thereof, an analyte-binding protein or fragment thereof, a peptide, and combinations or derivatives thereof.

In a particular (but non-limiting) embodiment, the analyte-specific binder is a monoclonal antibody or fragment thereof, and the at least one disulfide bond is in a hinge region of the monoclonal antibody or fragment thereof.

In certain particular (but non-limiting) embodiments, the monoclonal antibody or fragment thereof is an anti-CA 19-9 monoclonal antibody or fragment thereof.

In certain particular (but non-limiting) embodiments, the conjugate includes at least one, at least two, at least three, at least four, or more labels directly or indirectly attached to the analyte-specific binder.

In certain particular (but non-limiting) embodiments, the conjugate produced by the method is further defined as having the structure of Formula XII, XIII, or XIV. In a particular (but non-limiting) embodiment, "A" in each of Formulas XII, XIII, or XIV may further be defined as having the structure of one of Formulas IV, V, or VI.

Certain non-limiting embodiments of the present disclosure are directed to a method of detecting a target analyte in a sample utilizing any of the conjugates disclosed or otherwise contemplated herein. In the method, a sample is combined, either simultaneously or wholly or partially sequentially, with one or more of any of the conjugates disclosed or otherwise contemplated herein to form a mixture, and the mixture is incubated under conditions that allow for binding of the conjugate to a target analyte present in the sample, thereby forming a complex; then, the complex is detected.

In particular (but non-limiting) embodiments of the method, a sample is combined, either simultaneously or wholly or partially sequentially, with the first and second reagents of the immunoassay kit described in detail herein above (i.e., a first reagent comprising a monoclonal antibody or fragment thereof having at least one DISFPD-AE directly or indirectly conjugated thereto and a second reagent comprising a solid phase labeled with a monoclonal antibody or fragment thereof) to form a mixture. The mixture is then incubated under conditions that will allow for binding of the first reagent and the second reagent to any target analyte present in the sample, thereby forming a complex. That is, each of the analyte-specific binders of the first and second reagents specifically binds to an epitope of the target analyte, and the epitopes do not substantially overlap, such that the two analyte-specific binders can bind to the same target analyte molecule. The complex of first reagent-target analyte-second reagent is then detected by any method known in the art.

Any sample for which an assay for the presence of a biomarker (such as, but not limited to, a cancer biomarker such as CA 19-9) is desired can be utilized as the sample in accordance with the methods of the present disclosure. Non-limiting examples of samples include a biological sample such as, but not limited to, whole blood or any portion thereof (i.e., plasma or serum), urine, saliva, sputum, cerebrospinal fluid (CSF), skin, intestinal fluid, intraperitoneal fluid, cystic fluid, sweat, interstitial fluid, extracellular fluid, tears, mucus, bladder wash, semen, fecal, pleural fluid, nasopharyngeal fluid, and combinations thereof. Particular non-limiting examples include lysed whole blood cells and lysed red blood cells.

As mentioned above, the various components of the method are provided in combination (either simultaneously or sequentially). When the various components of the method are added sequentially, the order of addition of the components may be varied; a person having ordinary skill in the art can determine the particular desired order of addition of the different components to the assay. The simplest order of addition, of course, is to add all the materials simultaneously and determine the signals produced therefrom. Alternatively, each of the components, or groups of components, can be combined sequentially. In certain embodiments, an incubation step may be involved subsequent to one or more additions.

The conditions under which the mixture is incubated can vary widely, so long as the complex is formed under such conditions. Immunoassays based on a sandwich assay format are widely performed and immunoassay conditions are well known in the art; thus, selection of appropriate assay conditions is well within the purview of a person having ordinary skill in the art, and thus no further description thereof is deemed necessary.

The particular detection method utilized can vary widely, so long as the complex can be detected under such methods. Detection of complexes formed in a sandwich assay format are widely performed, and the detection procedures are well known in the art; thus, selection of appropriate detection methods is well within the purview of a person having ordinary skill in the art, and thus no further description thereof is deemed necessary.

The method may further include one or more additional steps to increase the accuracy and/or precision of the assay. For example (but not by way of limitation), the method may further include one or more wash steps for removing unbound (or non-specifically bound) reagent from the reaction prior to detection of complex formation.

Certain additional non-limiting embodiments of the present disclosure are directed to a microfluidics device that includes the components of any of the immunoassay kits described herein above. In particular, certain non-limiting embodiments include a microfluidics device for detecting CA 19-9 antigens in a sample. The microfluidics device comprises (i) an inlet channel through which a sample is applied; and (ii) at least a first compartment capable of being in fluidic communication with the inlet channel. The compartment(s) of (ii) contains the first and second reagents of the immunoassay kit described in detail herein above.

In certain non-limiting embodiments, the first and second reagents (as well as any additional elements, as described herein above) of (ii) are present in the same compartment. In alternative non-limiting embodiments, the first and second reagents (as well as any additional elements, as described herein above) are split between two or more compartments.

The device may be provided with any arrangement of the compartments and distribution of the various components therebetween that allows the device to function in accordance with the present disclosure.

Any of the compartments of the microfluidics device may be sealed to maintain reagent(s) disposed therein in a substantially air tight environment until use thereof; for example, compartments containing lyophilized reagent(s) may be sealed to prevent any unintentional reconstitution of the reagent. The inlet channel and a compartment, as well as two compartments, may be described as being "capable of being in fluidic communication" with one another; this phrase indicates that each of the compartment(s) may still be sealed, but that the two compartments are capable of having fluid flow therebetween upon puncture of a seal formed therein or therebetween.

The microfluidics devices of the present disclosure may be provided with any other desired features known in the art or otherwise contemplated herein. For example but not by way of limitation, the microfluidics devices of the present disclosure may further include a read chamber; the read chamber may be any of the compartments containing one or more of the reagents described herein above, or the read chamber may be in fluidic communication with said compartment(s) containing one or more reagents. The microfluidics device may further include one or more additional compartments containing other solutions, such as (but not limited to) wash solutions, dilution solutions, excipients, interference solutions, positive controls, negative controls, quality controls, and the like. These additional compartment(s) may be in fluidic communication with one or more of the other compartments. For example, the microfluidics device may further include one or more compartments containing a wash solution, and these compartment(s) may be capable of being in fluidic communication with any other compartment(s) of the device. In another example, the microfluidics device may further include one or more compartments containing an excipient for dissolution of one or more dried reagents, and the compartment(s) may be capable of being in fluidic communication with any other compartment(s) of the device. In yet a further example, the microfluidics device may include one or more compartments containing a dilution solution, and the compartment(s) may be capable of being in fluidic communication with any other compartment(s) of the device.

EXAMPLE

An Example is provided hereinbelow. However, the present disclosure is to be understood to not be limited in its application to the specific experimentation, results, and laboratory procedures disclosed herein. Rather, the Example is simply provided as one of various embodiments and are meant to be exemplary, not exhaustive.

Background: An immunoassay for the detection of cancer marker CA 19-9 employing an antibody-HEG-DMAE conjugate using NHS chemistry was previously developed for the Siemens ADVIA® Centaur analyzer, but the assay sensitivity, accuracy, and ambient temperature effect (ATE) require improvement. Therefore, the present Example involved the design and production of new assay reagents that provide more robust assay performance.

In this Example, a series of conjugates including the CA 19-9-MAb-MCC-HEG-DMAE, CA 19-9-MAb-TEG-TS-PAE, CA 19-9-MAb-disulfidepyridazinedione (DISFPN-HEG-DMAE, and CA 19-9-MAb-DISFPD-TEG-TSPAE were synthesized. All CA 19-9-MAb-AEs were evaluated on the Siemens ADVIA® Centaur using a sandwich assay format (FIG. 1).

In a non-limiting embodiment, the ADVIA® Centaur CA 19-9 assay is a two-step sandwich immunoassay using direct chemiluminometric technology which uses a single monoclonal antibody, 1116-NS-19-9, for both the Solid Phase and Lite Reagent. The antibody was covalently coupled to paramagnetic particles in the Solid Phase, and the same clone of antibody was labeled with acridinium ester in the Lite Reagent. The system dispenses 75 μL of the sample into a cuvette, and then 4.75 minutes later, 350 μL of the Solid Phase was added. This mixture was incubated at 37° C. for 8.25 minutes followed by a wash step using Wash1 to remove excess unbound antigens. After the first wash, 100 μL of reagent water was added to resuspend the particles. Then 100 μL of Lite Reagent was reacted with the Solid Phase-bound CA 19-9 antigens for an additional 18-minute incubation, where it is washed again with Wash 1. Then 300 μL each of Acid Reagent and Base Reagent were added to the cuvette to initiate the chemiluminescent reaction. A direct relationship exists between the concentration of CA 19-9 present in a patient sample and the amount of relative light units (RLUs) detected by the system.

One particular (but non-limiting) conjugate, CA 19-9-MAb-DISFPD-HEG-DMAE, demonstrated promising performance in relation to new assay requirements and was chosen as the primary (but non-limiting) candidate conjugate for the prototype assay among the new conjugates. The present disclosure represents the first application of novel dibromopyridazinedione-acridinium ester (DiBrPD-AE) labels in diagnostic uses.

Figure 2:
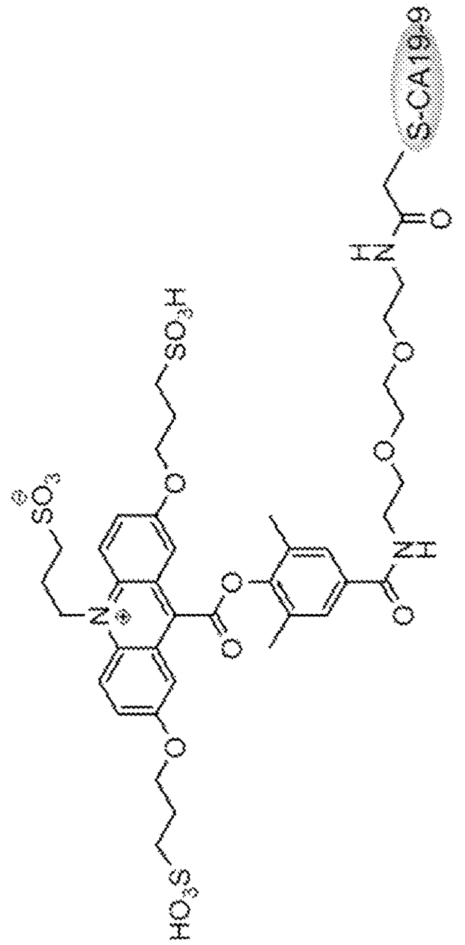
FIG. 2 schematically depicts the structures of two CA 19-9-MAb-AE conjugates: CA 19-9-MAb-MCC-HEG-DMAE and CA 19-9-MAb-TEG-TSPAE.
Figure 2:
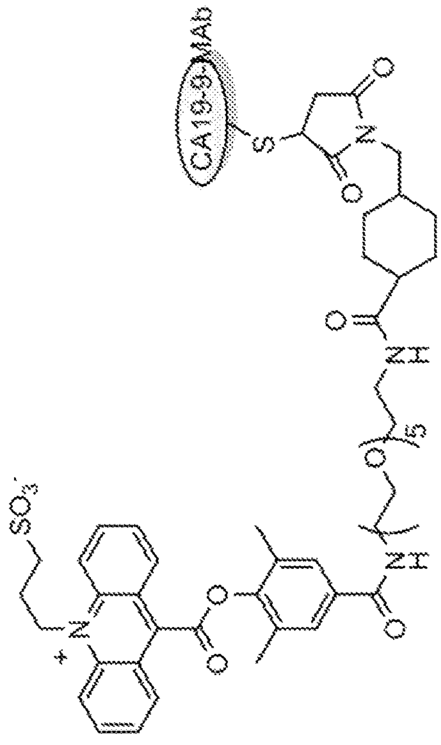

Reagent Design and Syntheses: The CA 19-9 immunoassay reagents in this Example included one solid phase (SP) and one lite reagent (FIG. 1). The solid phase reagent contains magnetic particles covalently labeled with monoclonal anti-CA 19-9 antibody. The lite reagent contains the CA 19-9-MAb-AE conjugate. Both solid and lite reagents form the sandwich assay. The synthesis of MAb-coated solid phase is a well-known and straight forward process, and therefore no further description thereof is deemed necessary. As such, this Example focuses on the synthesis of new CA 19-9-MAb-AE conjugates and their performance in a CA 19-9 immunoassay. In the current commercial ADVIA® Centaur CA 19-9 assay, the lite reagent is MAb-HEG-DMAE, which is prepared using amine-NHS chemistry. Since amine groups from the MAb are very sensitive to the antibody binding affinity, it is very challenging to reproduce the same AE conjugate for good assay performance. Thus, in the present Example, new MAb-AE conjugates were designed using sulfhydryl chemistry (FIG. 2). It is a general consensus that using sulfhydryl located in the hinge region of MAb for conjugation should not interfere with the MAb binding site, and the resulting conjugate may even have better immunoassay performance. Based on this thought, conjugates were prepared as follows.

Figure 5:
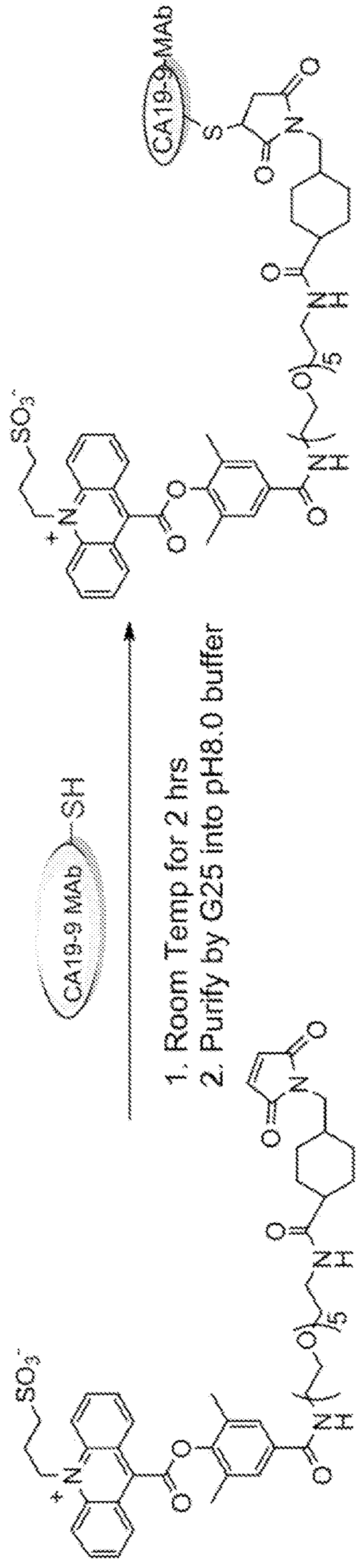
FIG. 5 schematically depicts the synthesis of the CA 19-9-MAb-MCC-HEG-DMAE conjugate of FIG. 2.

A compound containing maleimide groups, MCC-HEG-DMAE, was initially selected to prepare a CA 19-9-MAb conjugate using thiol chemistry for early study (FIG. 5). CA 19-9 MAb (Fujirebio Diagnostics Inc., 7.6 mg/mL, 12 mg) was buffer exchanged with a NAP25 column using a buffer (50 mM borate, 5 mM EDTA, pH 8.0), then the MAb solution was concentrated to 5 mg/mL using an Amicon Ultra centrifugal filter (Millipore, Ultracef-30K). DL-dithiothreitol (DTT, 99.0%, 6.83 mg) was dissolved in 1.69 mL of buffer (50 mM borate, 5 mM EDTA, pH 8.0) to make a 4.0 mg/mL solution. The DTT solution (0.0474 mL) was added into MAb (5.768 mg) solution with a DTT total concentration (1 mM) in the reaction mixture. The reaction mixture was incubated at 21° C. for 1.5 hours and then purified by a NAP25 column over a buffer (0.1 M phosphate, 300 mM NaCl, 5 mM EDTA, pH 7.0). DMAE-HEG-MCC (77.9 μL at 2.5 mM in DMSO) was added to the CA 19-9 antibody (2.922 mg) with a 10 to 1 molar ratio of reagent to antibody. The reaction vial was wrapped with an alumina foil, rocked at 21° C. for two hours, and then quenched with a freshly prepared buffer solution (0.1 M NEM, 39 μL in 0.1 M PBS EDTA pH7.0). The resulting conjugate was purified by a Sephadex G-25 column using a buffer (20 mM Phosphate, 150 mM NaCl, pH 8.0).

Figure 6:
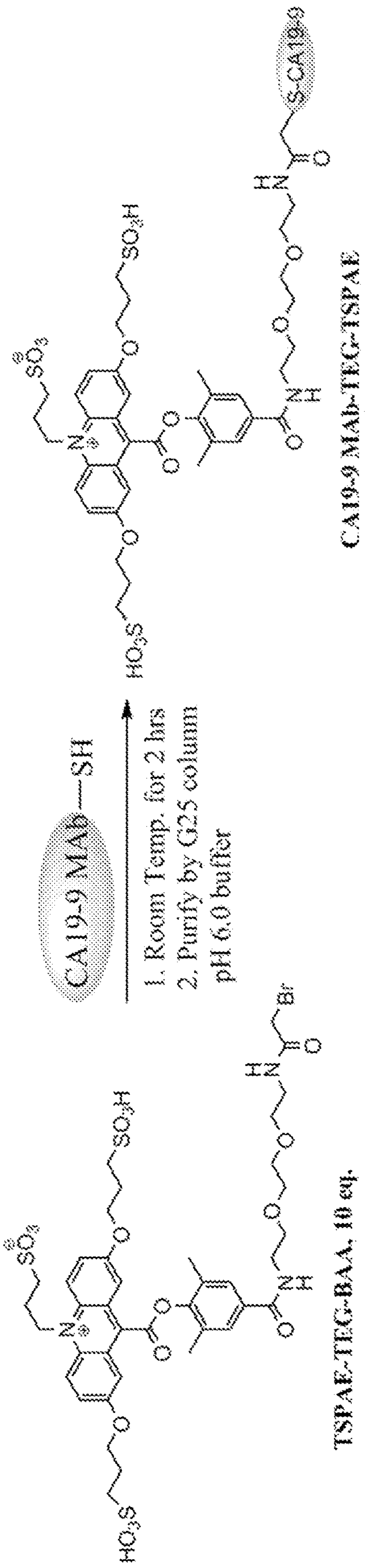
FIG. 6 schematically depicts the synthesis of the CA 19-9-MAb-TEG-TSPAE conjugate of FIG. 2.

Early data indicated that the CA 19-9-MAb-HEG-DMAE conjugate yielded a good assay curve. Given this initial encouraging performance, CA 19-9-MAb-TEG-TSPAE conjugates were also prepared using the same chemistry (FIG. 6). CA 19-9 MAb (Fujirebio Diagnostics Inc., 7.6 mg/mL, 12 mg) was buffer exchanged with a NAP25 column using a buffer (50 mM borate, 5 mM EDTA, pH 8.0), then the MAb solution was concentrated to 5 mg/mL using an Amicon Ultra centrifugal filter (Millipore, Ultracef-30K). DL-dithiothreitol (DTT, 6.83 mg) was dissolved in 1.69 mL of buffer (50 mM borate, 5 mM EDTA, pH 8.0) to make a 4.0 mg/mL solution. The DTT solution (0.0474 mL) was added into MAb (5.768 mg) solution with a DTT total concentration (1 mM) in the reaction mixture. The reaction mixture was incubated at 21° C. for 1.5 hours and then purified by a NAP25 column over a buffer (0.1 M phosphate, 300 mM NaCl, 5 mM EDTA, pH 7.0). TSPAE-TEG-BAA (30.0 μL at 2.5 mM in DMSO) was added to the CA 19-9 antibody (2.253 mg) with a 5 to 1 molar ratio of reagent to antibody. The reaction vial was wrapped with an alumina foil, rocked at 21° C. for two hours, and then quenched with a freshly prepared buffer solution (0.1 M NEM, 16.8 μL in 0.1 M PBS EDTA pH7.0). The resulting conjugate was purified by a Sephadex G-25 column using a buffer (50 mM Phosphate, 150 mM NaCl, pH 6.0).

However, both CA 19-9-MAb-MCC-HEG-DMAE and CA 19-9-MAb-TEG-TSPAE conjugates have either unfavorable ambient temperature effort (ATE) and/or a precision issue in assay performance.

Figure 3:
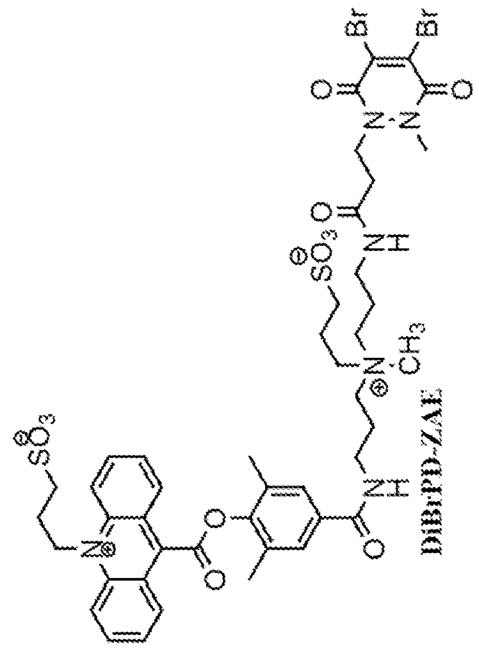
FIG. 3 schematically depicts the structures of five different dibromopyridazinedione-acridinium ester (DiBrPD-AE) labels designed and synthesized in accordance with the present disclosure.
Figure 3:
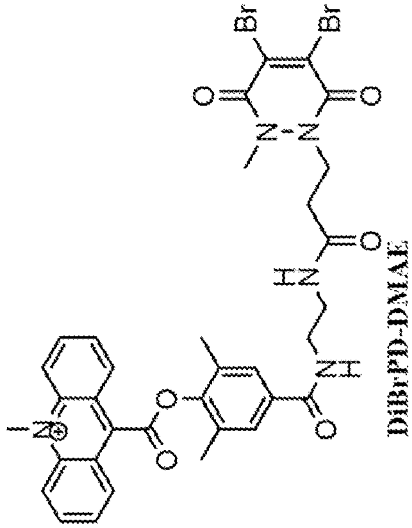
Figure 3:
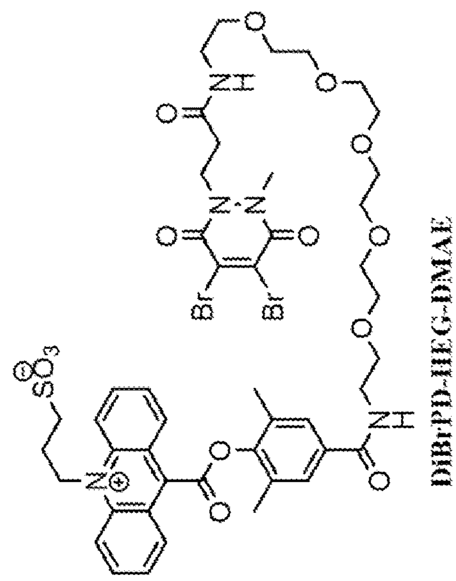
Figure 3:
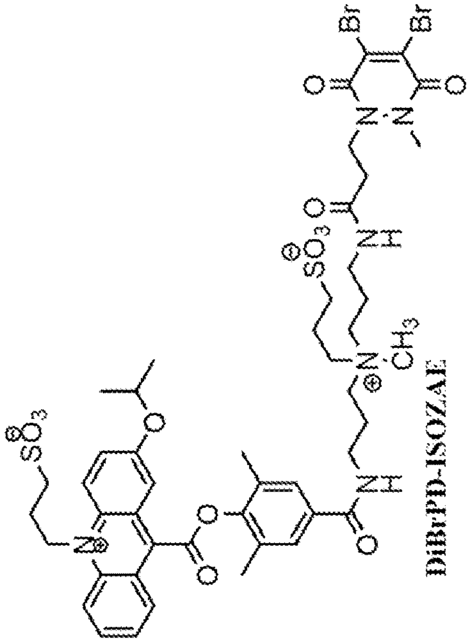
Figure 3:
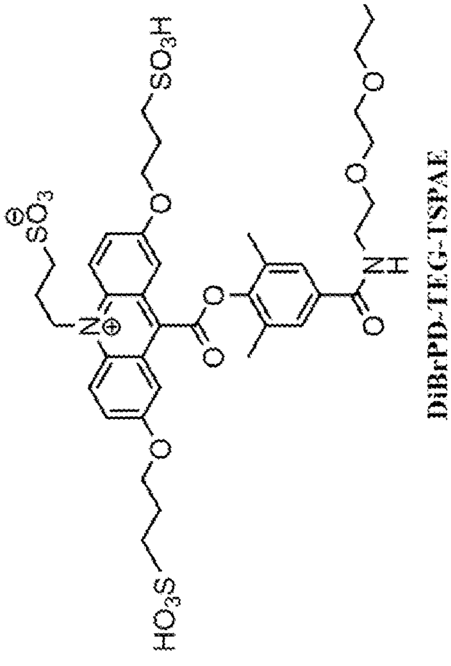
Figure 7:
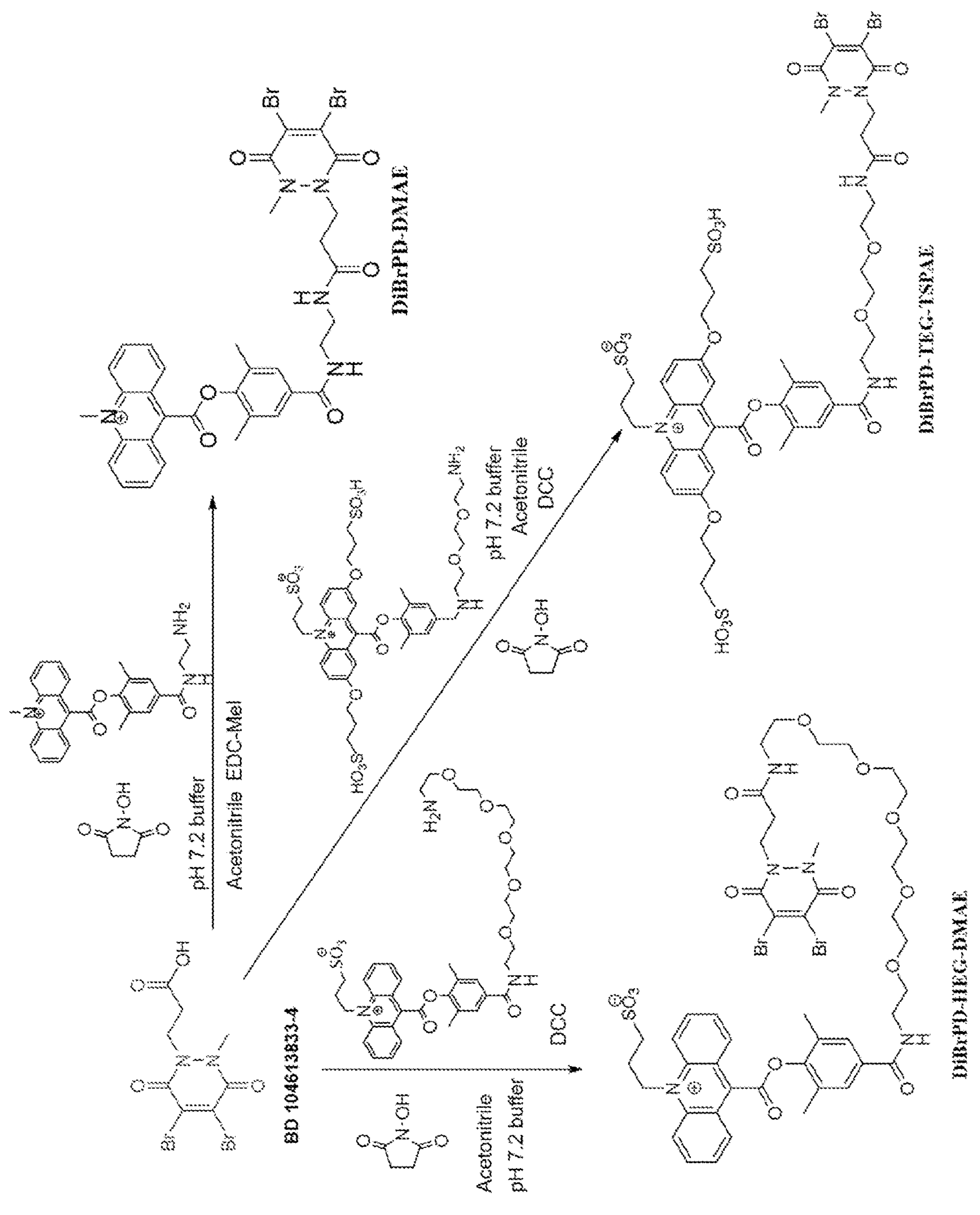
FIG. 7 schematically depicts the syntheses of three of the DiBrPD-AE labels of FIG. 3.
Figure 8:
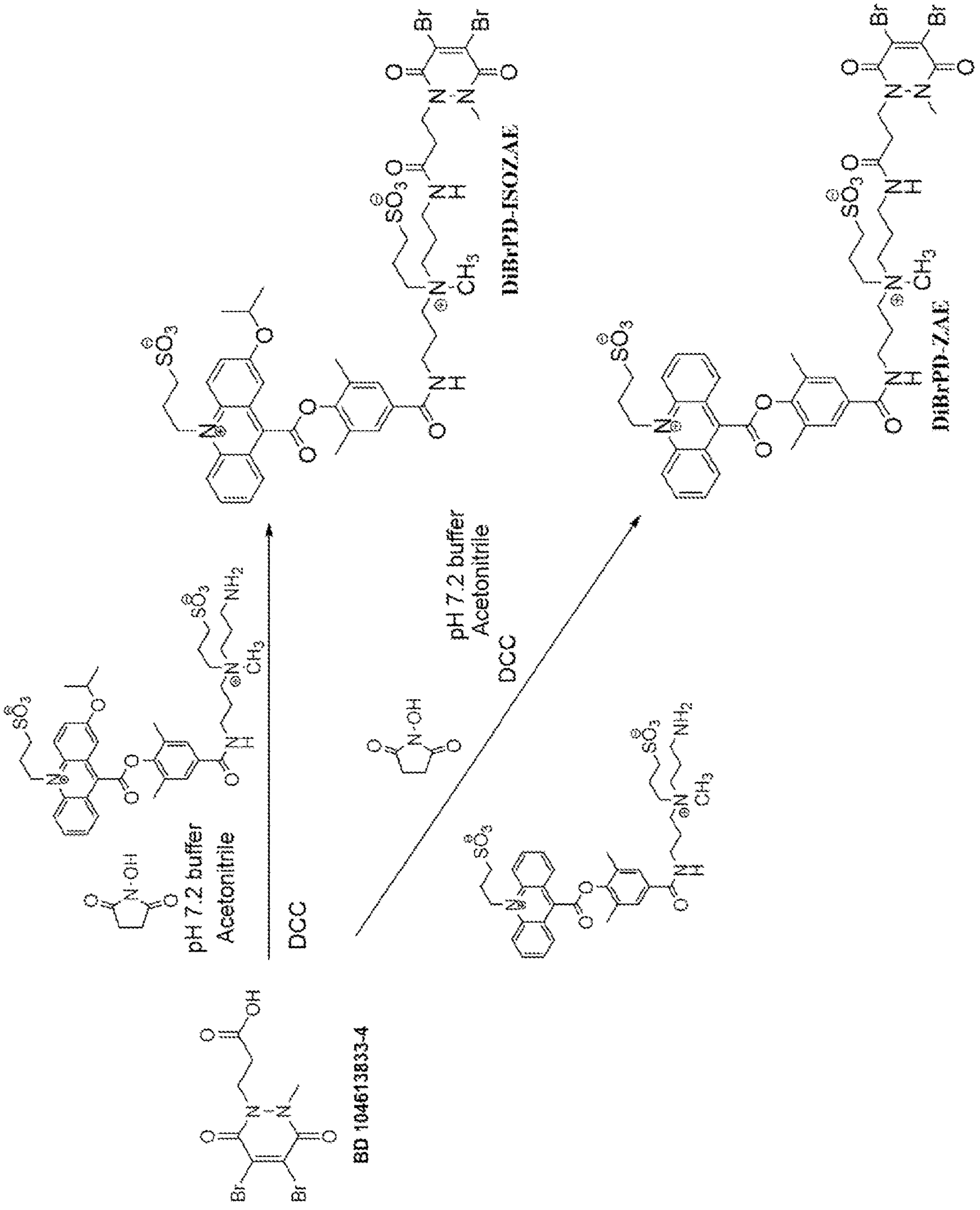
FIG. 8 schematically depicts the synthesis of the other two DiBrPD-AE labels of FIG. 3.

Most recently, Antibody-Drug-Conjugates (ADC) using functionalized dibromopyridazinediones have been reported in pharmaceutical research. It is suggested that by holding the reduced intact antibody together in conjugation through new sulfhydryl chemistry could better preserve the binding affinity and long-term stability of these ADC for therapeutic uses. However, this conjugation technique has not been explored for use in the diagnostic industry. Therefore, the inventors hypothesized that this bio-conjugation technique could be applied in the preparation of diagnostic assay reagents in accordance with the present disclosure. Thus, a series of new DiBrPD AEs such as (but not limited to) DiBrPD-HEG-DMAE, DiBrPD-TEG-TSPAE, DiBrPD-DMAE, DiBrPD-ZAE, and DiBrPD-iso-ZAE were designed and synthesized (FIGS. 3 and 7-8). By using linkers DiBrPD-HEG-DMAE and DiBrPD-TEG-TSPAE, two new re-bridging conjugates, CA 19-9-MAb-DISFPD-HEG-DMAE and CA 19-9-MAb-DISFPD-TEG-TSPAE, were prepared for new CA 19-9 immunoassays.

Procedure for the production of DiBrPD-DMAE (FIG. 7): DiBrPD (BD104613833-4) (16.2 mg, 45.5 μmol) was dissolved in Acetonitrile (0.5 mL). EDC·$CH_3I$ (27.0 mg, 91.0 μmol) and NHS (7.0 mg, 60.7 μmol) were added. The reaction mixture was stirred at room temperature for 30 minutes and then cooled to 0° C. The reaction mixture was added slowly to a solution of DMAE-ED (13.0 mg, 30.3 μmol) in Acetonitrile (1.0 mL) and pH 7.2 buffer (1.0 mL) at 0° C., and the reaction was allowed to incubate at 0° C. for 1 h. Then, the reaction temperature was gradually raised to room temperature. The reaction was monitored by an analytical HPLC. The crude reaction mixture was purified via a preparative HPLC (Phenomenex, Luna $C_{18}(2)$, 250×30 mm, 5 mm, 260 nm, 20 ml/min, 20-60%/40 min, 60-100%/5 min, 100% B/15 min.; A: Water+0.05% TFA; B: Acetonitrile+0.05% TFA). The desired product fractions were collected, frozen at a temperature at or below −70° C., and lyophilized. The desired product DiBrPD-DMAE (5.1 mg yellow powder, 16% yield) was obtained in 91% purity. MH+: 764.31, 766.42. Analytical HPLC: 6.4 minutes. Phenomenex, Kinetex C18, 50×4.6 mm, 2.6 um, 100 A, $10^{-50}$%/10 min, 1 ml/min, 260 nm.; A: Water+0.05% DFA; B: Acetonitrile+0.05% DFA.

Procedure for the production of DiBrPD-TEG-TSPAE (FIG. 7): DiBrPD (BD104613833-4) (7.1 mg, 20.0 μmol) was dissolved in Acetonitrile (1 mL). DCC (6.2 mg, 30.0 μmol) and NHS (2.3 mg, 20.0 μmol) were added. The reaction mixture was stirred at room temperature for 30 minutes. The reaction mixture was added slowly to a solution of TSPAE-TEG-$NH_2$ (18.0 mg, 20.0 μmol) in pH 7.2 buffer (2 mL), and the reaction was allowed to incubate at room temperature for 1 h. The reaction was monitored by an analytical HPLC. A white precipitate was filtered. The crude filtrate was purified via a preparative HPLC (Phenomenex, Luna $C_{18}(2)$, 250×30 mm, 5 mm, 20 ml/min., 260 nm, 10-40%/40 min, 40-100%/5 min.; A: Water+0.05% TFA; B: Acetonitrile+0.05% TFA). The desired product fractions were collected, frozen at a temperature at or below −70° C., and lyophilized. The desired product DiBrPD-TSPAE (19.5 mg orange powder, 79% yield) was obtained in 100% purity. MH+: 1236.45; 1238.62; 1240.01. Analytical HPLC: 4.0 minutes. Phenomenex, Kinetex C18, 50×4.6 mm, 2.6 um, 100 A, $10^{-50}$%/10 min, 1 ml/min, 260 nm.; A: Water+0.1% DFA; B: Acetonitrile+0.1% DFA.

Procedure for the production of DiBrPD-HEG-DMAE (FIG. 7): DiBrPD (BD104613833-4) (7.5 mg, 21.2 μmol) was dissolved in Acetonitrile (1 mL). DCC (6.6 mg, 31.8 μmol) and NHS (2.4 mg, 21.2 μmol) were added. The reaction mixture was stirred at room temperature for 1 h. The reaction mixture was added slowly to a solution of NSP-DMAE-HEG-$NH_2$ (16.0 mg, 21.2 μmol) in DMF (0.5 mL) and pH 7.2 buffer (0.5 mL), and the reaction was allowed to incubate at room temperature for 2 h. The reaction was monitored by an analytical HPLC. A white precipitate was filtered. The crude filtrate was purified via a preparative HPLC (Phenomenex, Luna C18(2), 250×30 mm, 5 mm, 20 ml/min., 260 nm, $10^{-40}$%/40 min, 40-100%/5 min.; A: Water+0.05% TFA; B: Acetonitrile+0.05% TFA). The desired product fractions were collected, frozen at a temperature at or below −70° C., and lyophilized. The desired product DiBrPD-HEGAE (11.2 mg yellow powder, 48% yield) was obtained in 100% purity. MH+: 1092.31; 1094.34. Analytical HPLC: 6.2 minutes. Phenomenex, Kinetex C18, 50×4.6 mm, 2.6 um, 100 A, $10^{-50}$%/10 min, 1 ml/min, 260 nm.; A: Water+0.1% DFA; B: Acetonitrile+0.1% DFA.

Procedure for the production of DiBrPD-ISOZAE (FIG. 8): DiBrPD (BD104613833-4) (10.3 mg, 29.0 μmol) was dissolved in Acetonitrile (1.0 mL). DCC (10.9 mg, 52.7 μmol) and NHS (6.1 mg, 52.7 μmol) were added. The reaction mixture was stirred at room temperature for 16 h. The reaction mixture was added slowly to a solution of ISOZAE-NH2 (21.1 mg, 26.3 μmol) in DMF (0.5 mL) and pH 7.2 buffer (0.5 mL), and the reaction was allowed to incubate at room temperature for 2 h. The reaction was monitored by an analytical HPLC. A white precipitate was filtered. The crude filtrate was purified via a preparative HPLC (Phenomenex, Luna C18(2), 250×30 mm, 5 mm, 20 ml/min., 260 nm, $10^{-40}$%/40 min, 40-100%/5 min.; A: Water+0.05% TFA; B: Acetonitrile+0.05% TFA). The desired product fractions were collected, frozen at a temperature at or below −70° C., and lyophilized. The desired product DiBrPD-ISOZAE (12.0 mg orange powder, 40% yield) was obtained in 100% purity. MH+: 1137.31; 1139.09; MNa+: 1161.47. LC/MS: 5.6 minutes. Phenomenex, Kinetex C18, 50×4.6 mm, 2.6 um, 100 A, $10^{-50}$%/10 min, 1 ml/min, 260 nm.; A: Water+0.05% DFA; B: Acetonitrile+0.05% DFA.

Procedure for the production of DiBrPD-ZAE (FIG. 8): DiBrPD (BD104613833-4) (5.5 mg, 15.3 μmol) was dissolved in Acetonitrile (0.5 mL). EDC·$CH_3I$ (6.8 mg, 23.0 μmol) and NHS (2.2 mg, 19.2 μmol) were added. The reaction mixture was stirred at room temperature for minutes and then cooled to 0° C. The reaction mixture was added slowly to a solution of ZAE-NH2 (9.5 mg, 12.8 μmol) in Acetonitrile (1.0 mL) and pH 7.2 buffer (1.0 mL) at 0° C., and the reaction was allowed to incubate at 0° C. for 1 h. The reaction was monitored by an analytical HPLC. The crude reaction mixture was purified via a preparative HPLC (Phenomenex, Luna C18(2), 250×30 mm, 5 mm, 260 nm, 20 ml/min, $10^{-40}$%/40 min, 40-100%/5 min, 100% B/15 min.; A: Water+0.05% TFA; B: Acetonitrile+0.05% TFA). The desired product fractions were collected, frozen at a temperature at or below −70° C., and lyophilized. The desired product DiBrPD-ZAE (9.3 mg yellow powder, 67% yield) was obtained in 96% purity. MH+: 1079.45, 1081.20. Analytical HPLC: 4.5 minutes. Phenomenex, Kinetex C18, 50×4.6 mm, 2.6 um, 100 A, $10^{-50}$%/10 min, 1 ml/min, 260 nm.; A: Water+0.05% DFA; B: Acetonitrile+0.05% DFA.

CA 19-9-MAb-DISFPD-HEG-DMAE was prepared as follows (FIG. 9): CA 19-9 MAb (Fujirebio Diagnostics Inc., 9 mg, 7.6 mg/mL, 1.184 mL) was buffer exchanged with a NAP25 column using a buffer (50 mM borate, 0.15M NaCl, 5 mM EDTA, pH 8.0). Antibody was conjugated to DiBrPD-HEG-DMAE at a molar ratio of reagent to antibody of 10 to 1 in the presence of TCEP in a molar ratio of TCEP:Ab of 10:1. To the Ab (1.0 mg, 4.0 mL) was added DiBrPD-HEG-DMAE (26.7 LLL at 2.5 mM) dropwise, the mixture was rocked at 4-8° C. for 2 hours, then TCEP (3.82 μL, 5 mg/mL) was added. The reaction mixture was rocked at 4-8° C. for 16 hours and purified by a G25 column using a buffer (20 mM phosphate, 0.15 M NaCl, pH8.0).

CA 19-9-MAb-DISFPD-TEG-TSPAE was prepared as follows (FIG. 10): CA 19-9 MAb (Fujirebio Diagnostics Inc., 3 mg, 7.6 mg/mL, 0.40 mL) was buffer exchanged with a NAP10 column using a buffer (50 mM borate, 0.15M NaCl, 5 mM EDTA, pH 8.0). Antibody was conjugated to TSPAE-TEG-DiBrPD at a molar ratio of reagent to antibody of 10 to 1 in the presence of TCEP in a molar ratio of TCEP:Ab of 10:1. To the Ab (3.0 mg, 6.0 mL) was added TSPAE-TEG-DiBrPD (80 μl at 2.5 mM) dropwise, the mixture was rocked at 4-8° C. for 2 hours, then TCEP was added. The reaction mixture was rocked at 4-8° C. for 16 hours and purified by a G25 column using a buffer (50 mM MES, 0.15 M NaCl, pH6.0).

Figure 9:
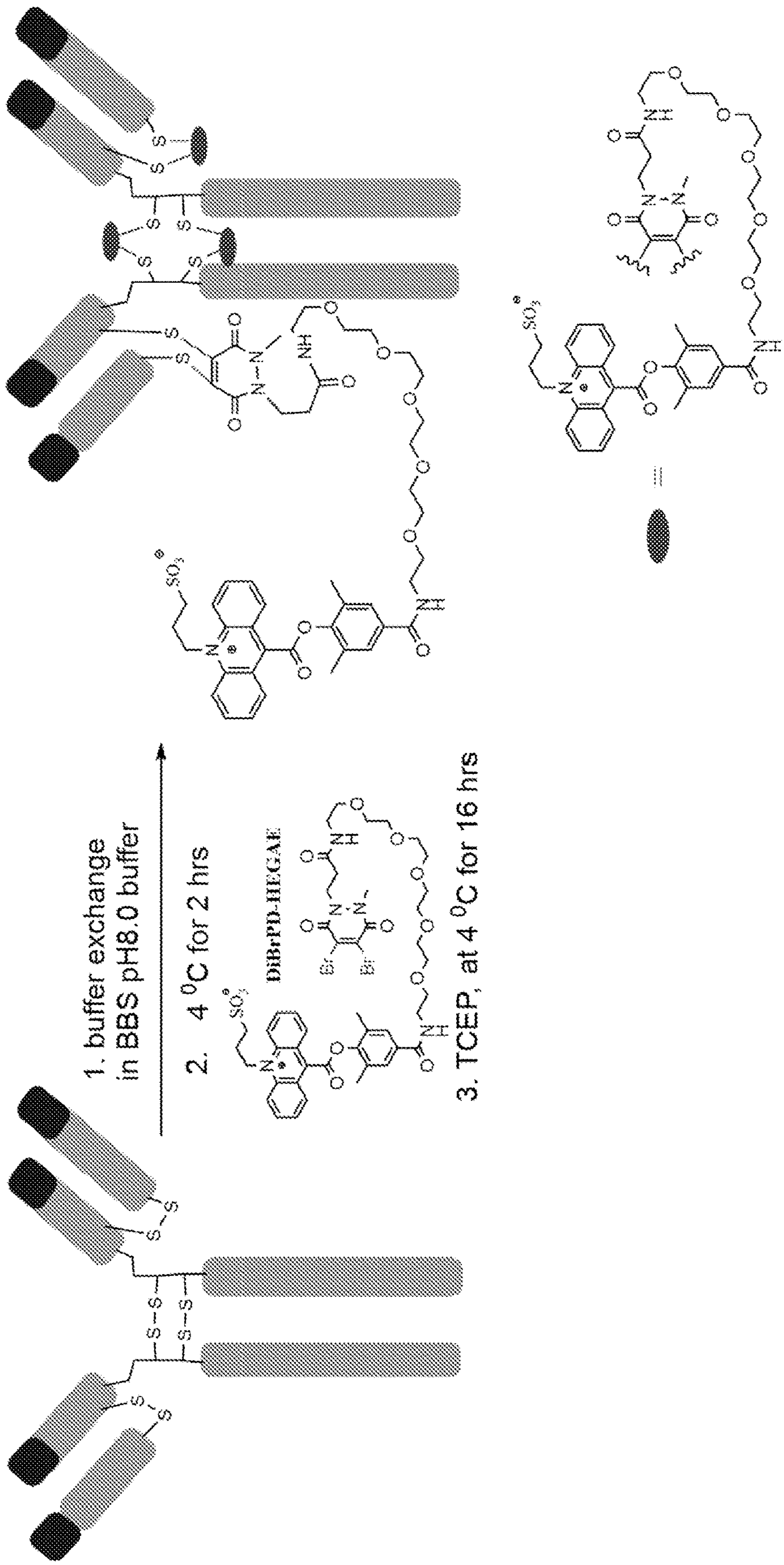
FIG. 9 schematically depicts the synthesis of the CA 19-9-MAb-DISFPD-HEG-DMAE conjugate of FIG. 4.
Figure 10:
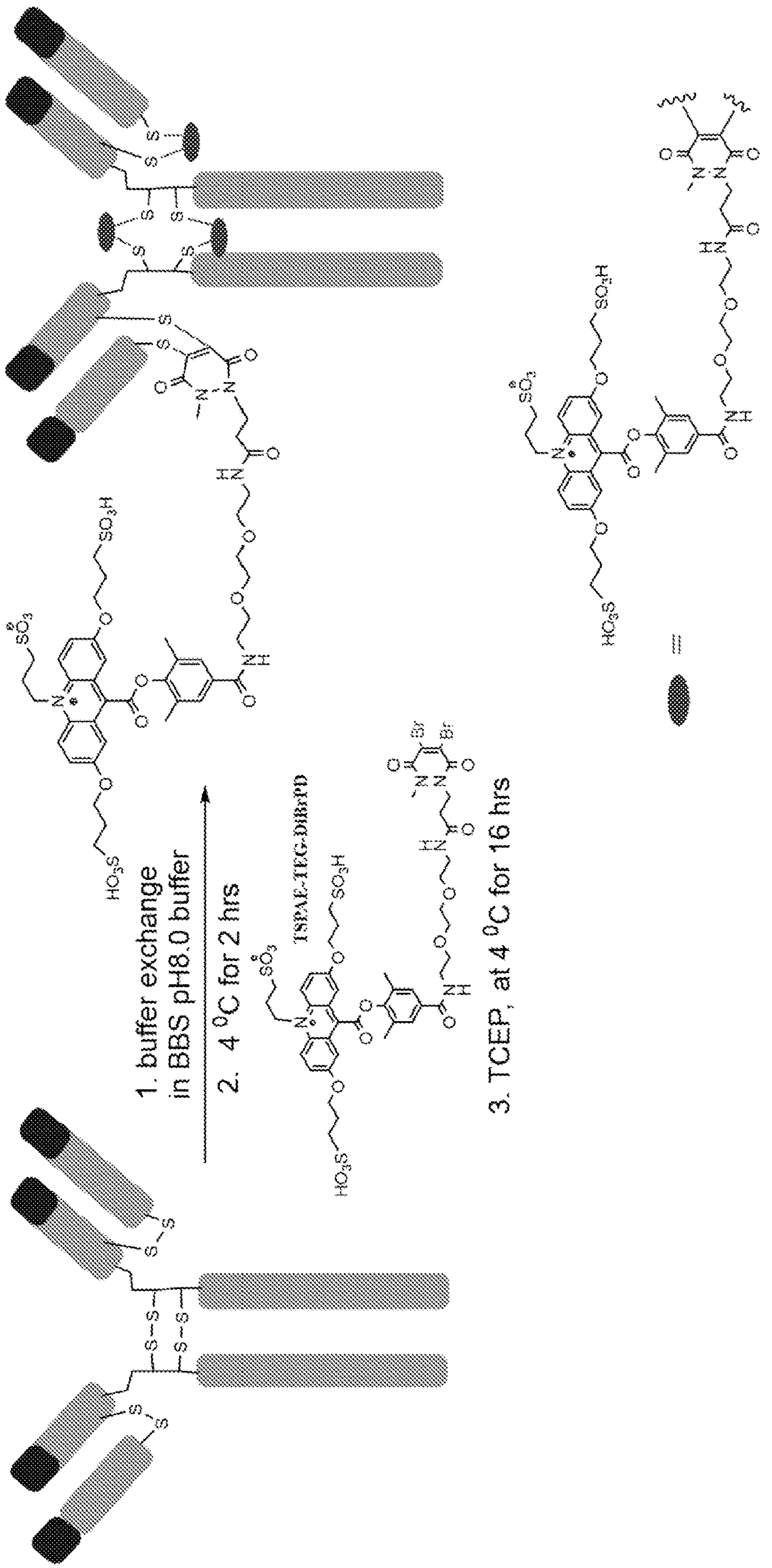
FIG. 10 schematically depicts the synthesis of the CA 19-9-MAb-DISFPD-TEG-TSPAE conjugate of FIG. 4.
Figure 11:
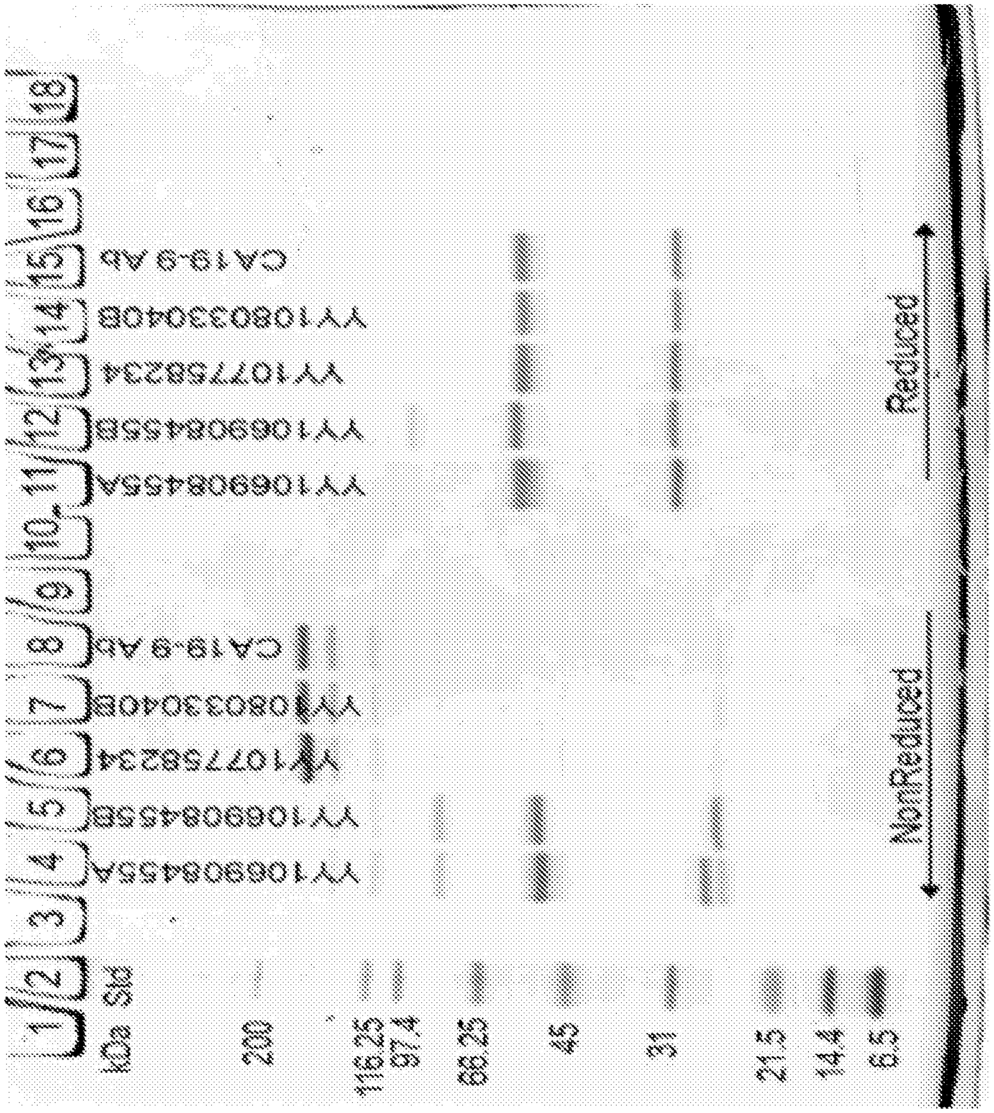
FIG. 11 contains a photograph of an SDS PAGE gel of four MAb-AE conjugates under non-reducing and reducing conditions. 4-20% criterion, TGX SDS PAGE, non-reducing and reducing, and BioSafe Coomassie stain. Lane 2—MW Standard. Lane 4—YY106908455A: CA 19-9 MAb MCC HEG-DMAE. Lane 5—YY106908455B: CA 19-9 MAb BAA TSPAE. Lane 6—YY107758234: CA 19-9 MAb DISFPD TSPAE. Lane 7—YY108033040B: CA 19-9 MAb DISFPD HEG-DMAE. Lane 8—CA 19-9 MAb alone. Lane 11—Reduced YY106908455A. Lane 12—Reduced YY106908455B. Lane 13—Reduced YY107758234. Lane 14—Reduced YY108033040B. Lane 15—Reduced CA 19-9 Ab.

The bio-conjugation processes of CA 19-9-MAb-DISFPD-HEG-DMAE and CA 19-9-MAb-DISFPD-TEG-TSPAE are displayed in FIGS. 9-10. FIG. 11 shows the SDS PAGE-Coomassie Gels of all four conjugates. In addition, the performance of all conjugates will be discussed hereinafter in the assay section.

Siemens ADVIA® Centaur CA 19-9 Immunoassay Performance: Evaluation of the CA 19-9-MAb-AE conjugates was carried out using the ADVIA® Centaur XP automated immunoassay analyzer, available from Siemens Healthcare Diagnostics Inc. (Tarrytown, NY). The binding curves and precision of four different conjugates were determined using a prototype CA 19-9 immunoassay employing a two-step format (see FIG. 1), largely similar to the current commercial ADVIA® Centaur CA 19-9 assay. Paramagnetic particles coated with CA 19-9 antibody (clone 1116N519-9) in DIPSO (3-(N,N-Bis[2-hydroxyethyl]amino)-2-hydroxypropanesulfonic acid) buffer at pH 7.6 served as the solid phase and was reacted with the sample in step 1, followed by magnetic separation and washing. The conjugates were added in step 2 at a concentration of 0.4 μg/mL in a DIPSO buffer at pH 7.6, followed by incubation, magnetic separation, and quantitative measurement of the chemiluminescent signal.

Figure 12:
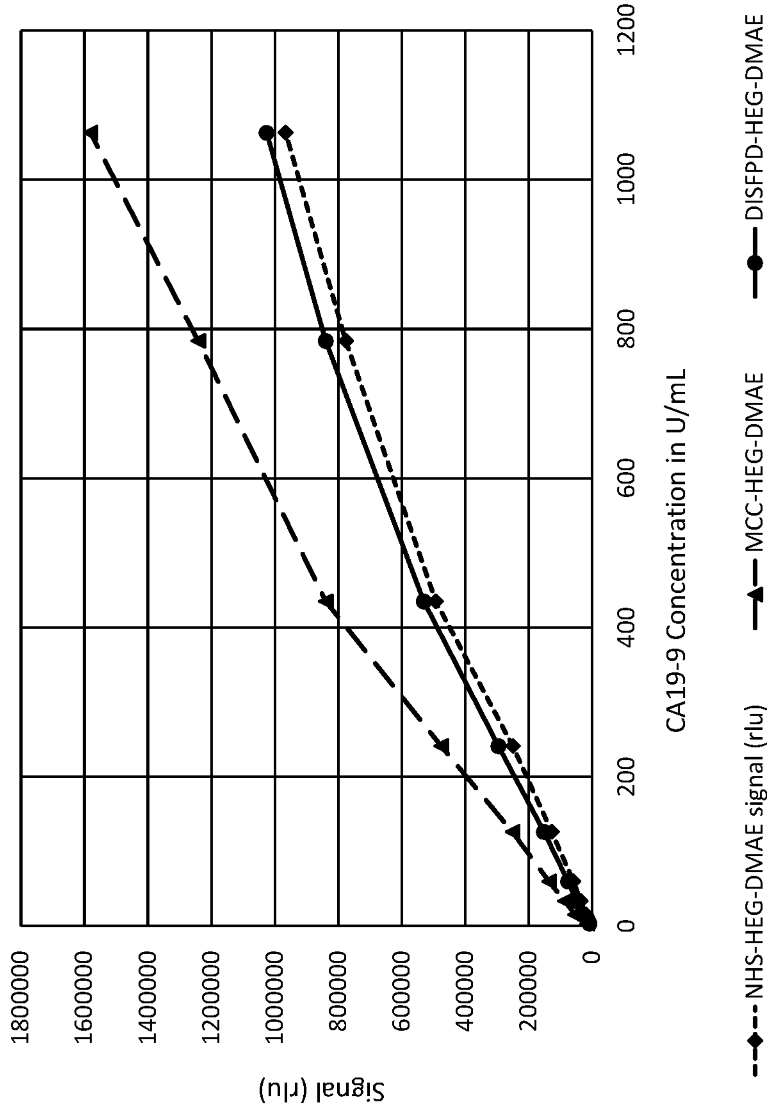
FIG. 12 graphically illustrates the standard curves generated using CA 19-9-MAb-X-HEG-DMAE conjugates with different linker chemistries (where “X” is NHS, MCC, and DISFPD). Binding curves were generated using paramagnetic particles coated with CA19-9 antibody (clone 1116N519-9) and antibody conjugates containing AE labels of NHS-HEG-DMAE, MCC-HEG, and DISFPD-HEG-DMAE.

With respect to FIG. 12, the binding curve and signal ratio data were generated for the CA19-9-MAb-X-HEG-DMAE conjugates by running a series of standards. The standards were made from a base of normal human serum that were spiked with CA19-9 antigen. The MCC-HEG-DMAE and DISFPD-HEG-DMAE conjugates were prepared and diluted to the same concentration of 0.4 μg/mL using the same buffer components and solid phase bulk. Both the solid phase and lite reagent buffers were made with DIPSO, EDTA Tetrasodium Salt, Gentamicin Sulfate, Amphotericin B, Normal Mouse Serum, Bovine Serum Albumin, Bovine Gamma Globulin, Sodium Azide, and Ecosurf EH-9. The lite reagent buffer also had Sodium Cholate. The NHS-HEG-DMAE conjugate was tested using commercial CA19-9 reagents. Each standard was run in replicates of 6 on an ADVIA Centaur XP instrument, and curves were generated by graphing signal versus mean concentration for each.

With respect to Table 1, the binding curve and signal ratio data were generated for the CA19-9-MAb-X-HEG-DMAE conjugates by running a series of standards. The MCC-HEG-DMAE and DISFPD-HEG-DMAE conjugates were prepared and diluted to the same concentration using the same buffer components and solid phase bulk. The NHS-HEG-DMAE conjugate was tested using commercial CA19-9 reagents. Each standard was run in replicates of 6 on an ADVIA Centaur XP instrument and curves were generated by graphing signal versus mean concentration for each. Signal ratios were determined by taking the lowest signal and dividing it by the second lowest signal (Standard 2/Standard 1) or the highest signal (Standard 9/Standard 1).

Curve shapes for the CA 19-9-MAb-NHS-HEG-DMAE, CA 19-9-MAb-MCC-HEG-DMAE, and CA 19-9-MAb-disulfidepyridazinedione (DISFPD)-HEG-DMAE were similar, with moderate differences in absolute signal. Signal ratios were highest for the DISFPD linked conjugates (FIG. 12 and Table 1).

With respect to Table 2, within-run precision for the CA19-9-MAb-X-HEG-DMAE conjugates was determined using the same reagents as described for Table 1. Samples included quality control materials and serum pool panels that span the assay range. Samples were run in replicates of 6 using each reagent and the within-run percent coefficient of variation (% CV) was determined for each. Mean % CV values for each reagent were calculated to determine the average precision across all samples.

Precision was the best for CA 19-9-MAb-DISFPD-HEG-DMAE, followed by CA 19-9-MAb-NHS-HEG-DMAE, and CA 19-9-MAb-MCC-HEG-DMAE (Table 2).

With respect to Table 3, ambient temperature effects for the NHS-HEG-DMAE and DISFPD-HEGG-DMAE were compared using the same reagents as described above. The testing was completed to determine the effect across the operating temperature of the instrument (18° C. to 30° C.). Two testing runs were completed at each temperature point, each repeated on 2 separate days. This resulted in a total of 12 runs completed over 6 testing days: 3 temperatures×2 runs per temperature (per day)×2 testing days. All samples were processed in a minimum of 3 replicates during each run. Data from these runs were averaged and a calibration curve was created at each temperature. These curves were then used to calculate the results from the other temperature runs. From these data, a percent bias was calculated as the difference between the high and low temperature results. Mean percent bias was determined as the percent bias across all temperature combinations for each sample.

With respect to Table 4, the standard curve thereof was generated with eight levels of standards, processed at 3 replicates each. The lite reagent consisted of 0.2 μg/mL CA19-9-MAb-TEG-TSPAE or 0.2 μg/mL CA19-9-MAb-DISFPD-HEG-DMAE. The solid phase reagent consisted of paramagnetic beads covalently coupled to monoclonal anti-CA 19-9 antibody (clone 1116-NS-19-9). Testing was performed using the ADVIA Centaur family of immunoassay analyzers. The coefficient of variation (% CV) was calculated to give the within-run precision of each conjugate and the median % CV value for all samples was determined.

With respect to Table 5, ambient temperature evaluation of the HEGAE-DISFPD and TSPAE-DISFPD Lite reagents was performed using the ADVIA Centaur family of immunoassay analyzers. The lite reagent consisted of 0.2 μg/mL CA19-9-MAb-DISFPD-HEG-DMAE or 0.1 μg/mL CA19-9-MAb-DISFPD-TEG-TSPAE. The solid phase reagent consisted of paramagnetic beads covalently coupled to monoclonal anti-CA 19-9 antibody (clone 1116-NS-19-9). Testing was done in a temperature chamber over the course of 2 days at 18° C. and 30° C. A standard curve was generated using eight levels of standards, processed at 3 replicates each. Signal (in RLU) was measured for a series of serum pools and QC samples at 4 replicates each and analyte was determined for each using the standard curve. Percent Bias was calculated as: ((CA19-9 (U/mL) at 18° C.)−(CA19-9 (U/mL) at 30° C.))/(Average CA19-9 (U/mL)). Overall mean, minimum, and maximum individual biases are shown.

In a separate study, the standard curves, signal ratios, and precision with CA 19-9-MAb-DISFPD-TEG-TSPAE conjugate was compared to CA 19-9-MAb-DISFPD-HEG-DMAE. The DISFPD-TEG-TSPAE monoclonal antibody conjugate gave much higher signal than the DISFPD-HEG-DMAE monoclonal antibody conjugate, although its signal/background ratios were slightly lower. Within-run precision was comparable for both within the limits of this study (Table 4).

Ambient temperature effects were measured on the same analyzer in a temperature-controlled chamber. A calibration curve was generated at 24° C. ambient temperature, and serum pools and QC were measured at 18° C. and 30° C. ambient temperature. These signals were converted to concentrations using the 24° C. curve, and the concentrations obtained were compared.

Ambient temperature effects were compared for the CA 19-9-MAb-DISFPD-HEG-DMAE and CA 19-9-MAb-NHS-HEG-DMAE conjugates. The CA 19-9-MAb-DISFPD-HEG-DMAE showed clearly superior performance over the prior art conjugate (Table 3).

In a separate experiment, the ambient temperature effect for the CA 19-9-MAb-DISFPD-TEG-TSPAE conjugate was compared to the CA 19-9-MAb-DISFPD-HEG-DMAE conjugate. The temperature effects for both were comparable, although the range of effects between individual serum pools was narrower for the DISFPD-HEG-DMAE conjugate (Table 5).

TABLE 1

Binding Curves and Signal Ratios for the CA 19-9-MAb-X-HEG-DMAE Conjugates (X = NHS, MCC, and DISFPD)

| Sample | Concentration (U/mL) | CA 19-9 Antibody-Acridinium Ester conjugate NHS-HEG-DMAE | MCC-HEG-DMAE | DISFPD-HEG-DMAE |
|---|---|---|---|---|
| | | signal (rlu) | | |
| Standard 1 | 3.3 | 9453 | 15139 | 7654 |
| Standard 2 | 15.1 | 18535 | 53621 | 29715 |
| Standard 3 | 33.3 | 36261 | 86025 | 49154 |
| Standard 4 | 59.6 | 58589 | 135807 | 75400 |
| Standard 5 | 126 | 126976 | 251160 | 151367 |
| Standard 6 | 241 | 249659 | 475544 | 295046 |
| Standard 7 | 435 | 492530 | 839609 | 530364 |
| Standard 8 | 784 | 776181 | 1241351 | 839174 |
| Standard 9 | 1063 | 966429 | 1581577 | 1025823 |
| ratio S2/S1 | | 2.0 | 3.5 | 3.9 |
| ratio S9/S1 | | 102 | 104 | 134 |

TABLE 2

Within-Run Precision for CA 19-9-MAb-X-HEG-DMAE Conjugates (X = NHS, MCC, and DISFPD)

| Sample | Concentration (U/mL) | CA 19-9 Antibody-Acridinium Ester conjugate NHS-HEG-DMAE | MCC-HEG-DMAE | DISFPD-HEG-DMAE |
|---|---|---|---|---|
| | | within-run precision (% CV) | | |
| QC-1 | 14.9 | 6.3% | 5.7% | 4.3% |
| QC-2 | 58.6 | 1.5% | 6.4% | 3.0% |

TABLE 2-continued

Within-Run Precision for CA 19-9-MAb-X-HEG-DMAE Conjugates (X = NHS, MCC, and DISFPD)

| Sample | Concentration (U/mL) | CA 19-9 Antibody-Acridinium Ester conjugate NHS-HEG-DMAE | MCC-HEG-DMAE | DISFPD-HEG-DMAE |
|---|---|---|---|---|
| | | within-run precision (% CV) | | |
| QC-3 | 195 | 2.5% | 6.5% | 2.6% |
| Serum Pool-1 | 7.47 | 7.8% | 2.6% | 2.9% |
| Serum Pool-2 | 21.9 | 5.2% | 1.6% | 2.4% |
| Serum Pool-3 | 34.5 | 7.6% | 3.1% | 3.6% |
| Serum Pool-4 | 99.4 | 2.2% | 3.7% | 2.0% |
| Serum Pool-5 | 324 | 2.3% | 5.4% | 4.6% |
| Serum Pool-6 | 644 | 2.0% | 6.0% | 2.2% |
| Average precision | | 4.1% | 4.5% | 3.1% |

TABLE 3

Ambient Temperature Effect for CA 19-9-MAb-X-HEG-DMAE Conjugates (X = NHS and DISFPD)
Ambient temperature effect: % Bias between 18° C. and 30° C., based on calibration at 24° C.

| | Conc. in U/mL | NHS-HEG-DMAE | DISFPD-HEG-DMAE |
|---|---|---|---|
| Serum Pool 2 | 24.3 | 59.9% | 19.7% |
| Serum Pool 3 | 38.9 | 53.3% | 24.7% |
| Serum Pool 4 | 104.0 | 36.4% | 7.4% |
| Serum Pool 5 | 343.9 | 12.6% | −9.5% |
| QC-2 | 629.6 | 47.1% | 16.3% |
| QC-3 | 64.1 | 41.0% | 13.7% |
| Max Bias | | 59.9% | 24.7% |
| Min Bias | | 12.6% | −9.5% |
| Mean Bias | | 41.7% | 12.1% |

TABLE 4

Standard Curves, Signal Ratios and Within-Run Precision for CA 19-9-MAb-TEG-TSPAE Compared to CA 19-9-MAb-DISFPD-HEG-DMAE Conjugate

| | Concentration in U/mL | HEGAE-DISFPD 0.2 μg/mL | TSPAE-DISFPD 0.2 μg/mL |
|---|---|---|---|
| Standard 1 | 0 | 1453 | 12306 |
| Standard 2 | 16.5 | 4481 | 35755 |
| Standard 3 | 37.8 | 9095 | 78720 |
| Standard 4 | 67 | 15894 | 144663 |
| Standard 5 | 129.9 | 34815 | 294491 |
| Standard 6 | 278.2 | 74341 | 636143 |
| Standard 7 | 489 | 139808 | 1128684 |
| Standard 8 | 777.8 | 218158 | 1700176 |
| S2/S1 | | 3.1 | 2.9 |
| S8/S1 ratio | | 150.1 | 138.2 |
| Median within-run precision | | 3.9% | 3.3% |

TABLE 5

Ambient Temperature Effect for CA 19-9-MAb-DISFPD-TEG-TSPAE Compared to CA 19-9-MAb-DISFPD-HEG-DMAE Conjugate

| | HEGAE-DISFPD 0.2 μg/mL | | | TSPAE-DISFPD 0.1 μg/mL | | |
|---|---|---|---|---|---|---|
| | STORED CALIBRATION: | | | | | |
| | 18° C. | | | 18° C. | | |
| | RUN TEMP: | | | | | |
| | 18° C. U/mL | 30° C. | % bias 18° C. vs 30° C. | 18° C. U/mL | 30° C. | % bias 18° C. vs 30° C. |
| POOL MDP5 | 135 | 134 | 0% | 136 | 163 | −19% |
| POOL C | 46 | 36 | 26% | 50 | 43 | 13% |
| POOL D | 55 | 49 | 11% | 59 | 45 | 28% |
| POOL J | 844 | 887 | −5% | 719 | 709 | 1% |
| QC 1 | 113 | 94 | 18% | 101 | 110 | −8% |
| MEAN | | | 12% | | | 8% |
| MIN | | | −5% | | | −19% |
| MAX | | | 26% | | | 28% |

Figure 4:
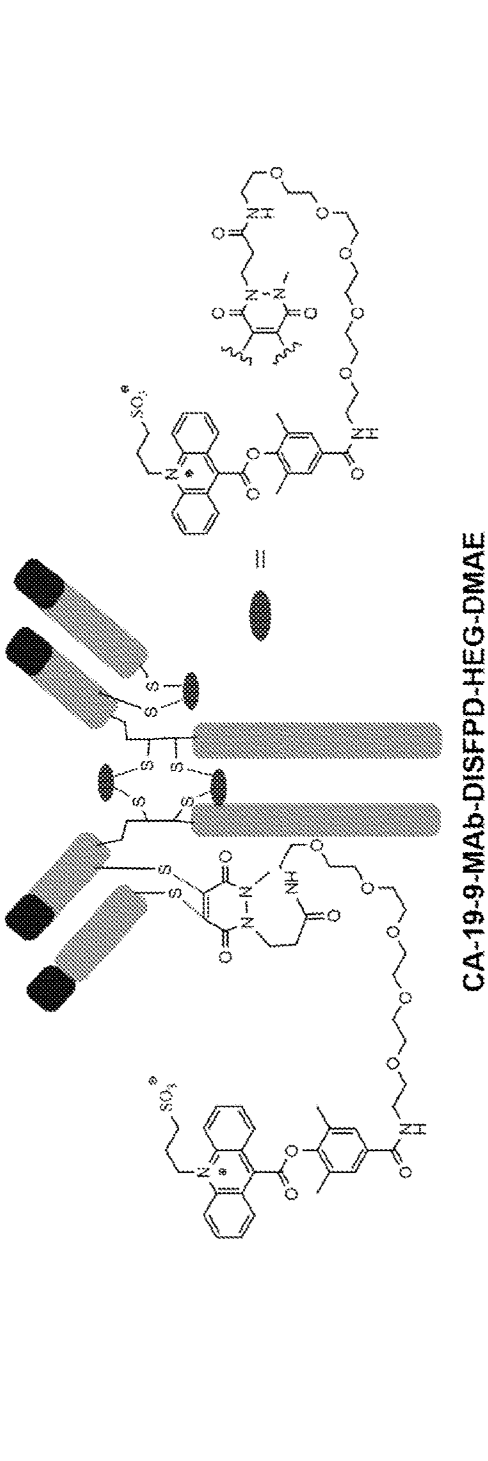
FIG. 4 schematically depicts the structures of two CA 19-9-MAb-AE conjugates constructed in accordance with the present disclosure: CA 19-9-MAb-DISFPD-HEG-DMAE and CA 19-9-MAb-DISFPD-TEG-TSPAE.
Figure 4:
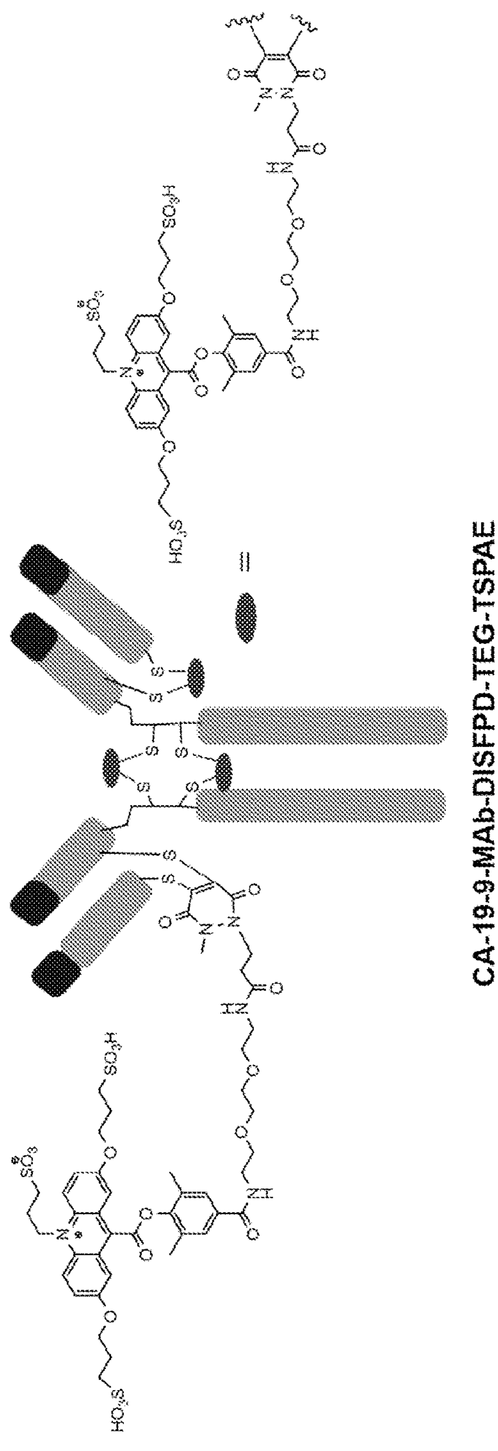

Conclusion: A series of new DiBrPD-AEs such as (but not limited to) DiBrPD-HEG-DMAE, DiBrPD-TEG-TSPAE, DiBrPD-DMAE, DiBrPD-ZAE, and DiBrPD-iso-ZAE were successfully designed and synthesized (FIG. 3). By using these novel DiBrPD-AE labels, new CA 19-9 MAb-AE conjugates (FIGS. 2 and 4) were also synthesized and evaluated for use in a new prototype CA 19-9 immunoassay (Tables 1-5; FIG. 12). Based on overall assay performance, multiple conjugates tested met the preliminary assay requirements (Tables 1-5), with (for example, but not by way of limitation) CA 19-9-MAb-DISFPD-HEG-DMAE (FIG. 9) being an excellent candidate for use in development of a commercial CA 19-9 immunoassay. This Example represents the first application of a novel DiBrPD-AE label in preparation of antibody conjugates in the diagnostic industry.

While certain embodiments described herein disclose the use of anti-CA 19-9 antibodies, it will be understood that the use of this particular antibody and target analyte is for purposes of example only. Rather, the binding of the DiBrPD-AE molecule to an antibody as described herein occurs in the hinge region of the antibody and thus is completely independent of the particular complementarity determining regions present. As such, the conjugation methods of the present disclosure can be utilized with any antibody or fragment thereof. Likewise, the use of the antibody conjugates in the particular sandwich immunoassay described herein is also for purposes of example only. The conjugates of the present disclosure can be utilized with any immunoassays known in the art or otherwise contemplated herein that utilize an antibody therein.

Thus, in accordance with the present disclosure, there have been provided compositions, kits, and devices, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A label:

of Formula I:

Formula I

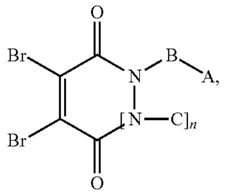

n = 1 or 0 wherein:

"A" is a chemiluminescent compound having the structure of Formula IV:

Formula IV

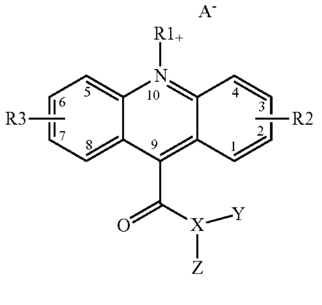

wherein:

"R1" is selected from the group consisting of:

an alkyl, alkenyl, alkynyl, or aralkyl group of 1 to 35 carbon atoms and 0 to 20 heteroatoms;

a sulfopropyl or sulfobutyl group; and a group —$R^a$—Z, where $R^a$ is a divalent radical selected from alkyl, alkenyl, alkynyl, aryl, or aralkyl group of 1 to 35 carbon atoms and 0 to 20 heteroatoms;

"R2" is placed at one or more of positions C1 to C4, and each "R2" is independently selected from the group consisting of hydrogen, alkyl, OR, OH, SR, SH, $NH_2$, and NR'R", wherein R, R', and R" are each independently selected from the group consisting of an alkyl, alkenyl, alkynyl, aryl, and aralkyl group, wherein each group contains 0 to 20 heteroatoms;

"R3" is placed at one or more of positions C5 to C8, and each "R3" is independently selected from the group consisting of hydrogen, alkyl, OR, OH, SR, SH, $NH_2$, and NR'R", wherein R, R', and R" are each independently selected from the group consisting of an alkyl, alkenyl, alkynyl, aryl, and aralkyl group, wherein each group contains 0 to 20 heteroatoms;

"X" is oxygen or nitrogen;

"Z" is omitted when "X" is oxygen and is $SO_2$—Y when "X" is nitrogen;

"Y" is a group selected from a halogenated or unhalogenated, branched or straight-chained alkyl group; a substituted or unsubstituted aryl group; and a heterocyclic ring group; wherein the "Y" group comprises 0 to 20 heteroatoms, and wherein the "Y" group further comprises a functional group that links to the spacer "B" of Formula I; and "A" is a counter ion selected from the group consisting of $CH_3SO_4^-$, $FSO_3^-$, $CF_3SO_4^-$, $C_4F_9SO_4^-$, $CH_3C_6H_4SO_3^-$, a halide, $CF_3COO^-$, $CH_3COO^-$, and $NO_3^-$;

"B" is a spacer selected from an alkyl, alkenyl, alkynyl, or aralkyl group, wherein the spacer contains 0 to 20 heteroatoms; and when n=1, "C" is a group comprising 1 to 40 carbon atoms and 0 to 20 heteroatoms.

2. The label of claim 1, wherein "A" of Formula I is a chemiluminescent compound having the structure of Formula V:

Formula V

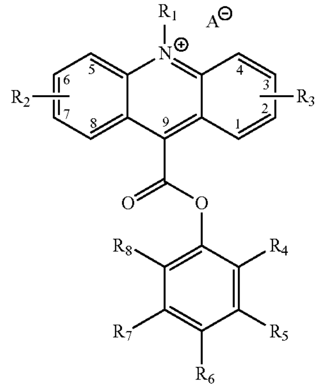

wherein:

each of "$R_4$" and "$R_8$" is independently selected from hydrogen or an alkyl, alkenyl, alkynyl, alkoxyl (—OR), alkylthiol (—SR), or substituted amino group;

each of "$R_5$," "$R_6$," and "$R_7$" is independently selected from hydrogen or an alkyl, alkenyl, alkynyl, aryl, or aralkyl group, wherein each group contains 0 to 20 heteroatoms; and one of "$R_5$," "$R_6$," and "$R_7$" further comprises a functional group that links to the spacer "B" of Formula I.

3. The label of claim 1, wherein "A" of Formula I is a chemiluminescent dimethylphenyl acridinium ester having the structure of Formula VI:

Formula VI

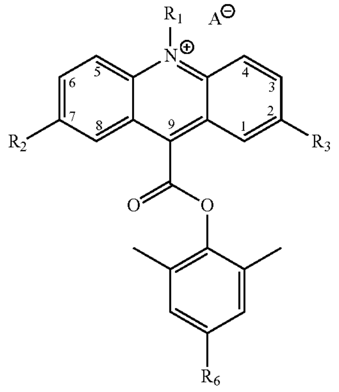

wherein:

"$R_1$" is a methyl or a sulfopropyl group;

each of "$R_2$" and "$R_3$" is independently selected from hydrogen or a methoxy, sulfopropyloxyl, or poly(ethylene)glycoloxy group; and "$R_6$" is an amide group (CONH—) connecting to the spacer "B" of Formula I.

4. The label of claim 1, having the structure of Formula VII:

Formula VII

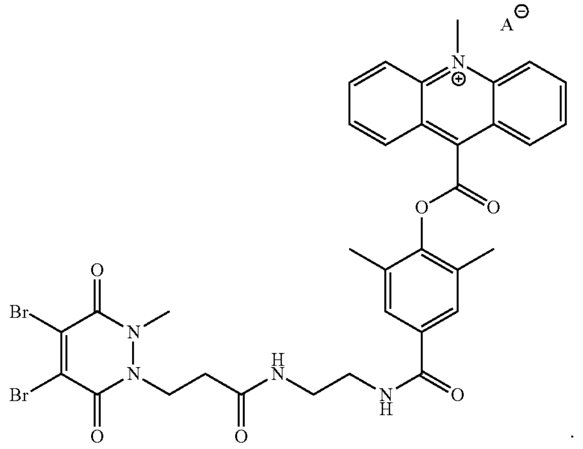

5. The label of claim 1, having the structure of Formula VIII:

Formula VIII

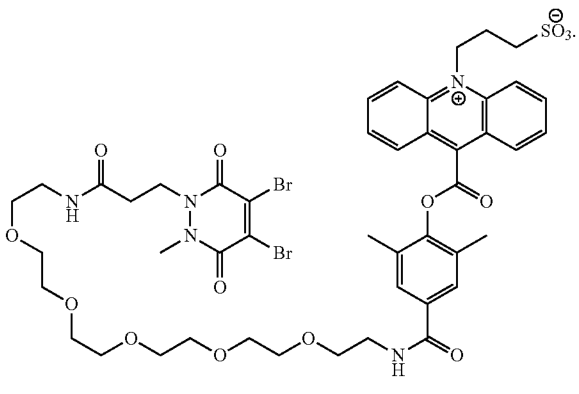

6. The label of claim 1, having the structure of Formula IX:
Formula IX
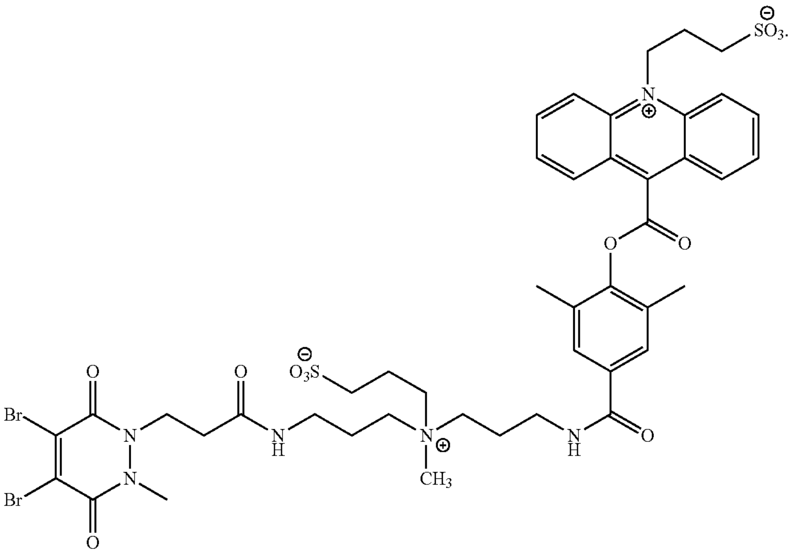
7. The label of claim 1, having the structure of Formula X:
Formula X
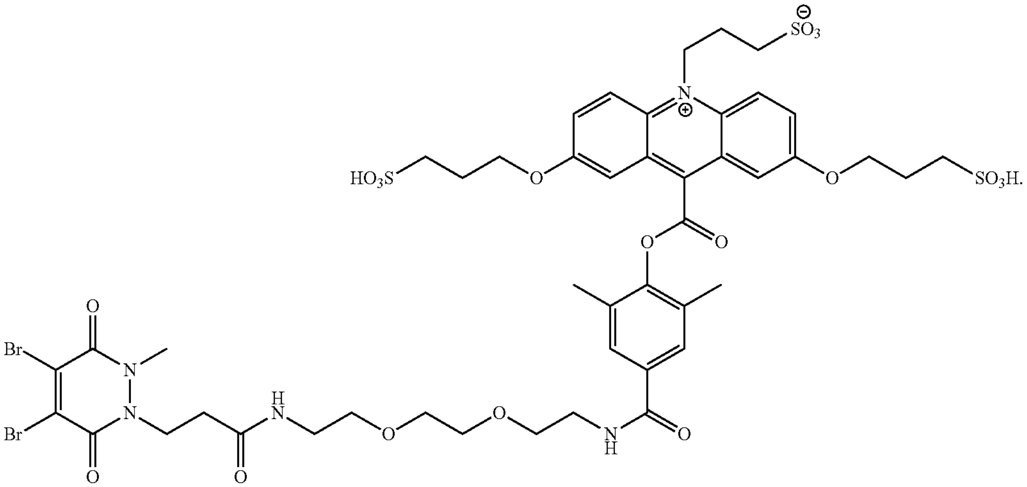

8. The label of claim 1, having the structure of Formula XI:

13. The conjugate of claim 9, wherein at least two labels directly or indirectly attached to the analyte-specific binder.

Formula XI

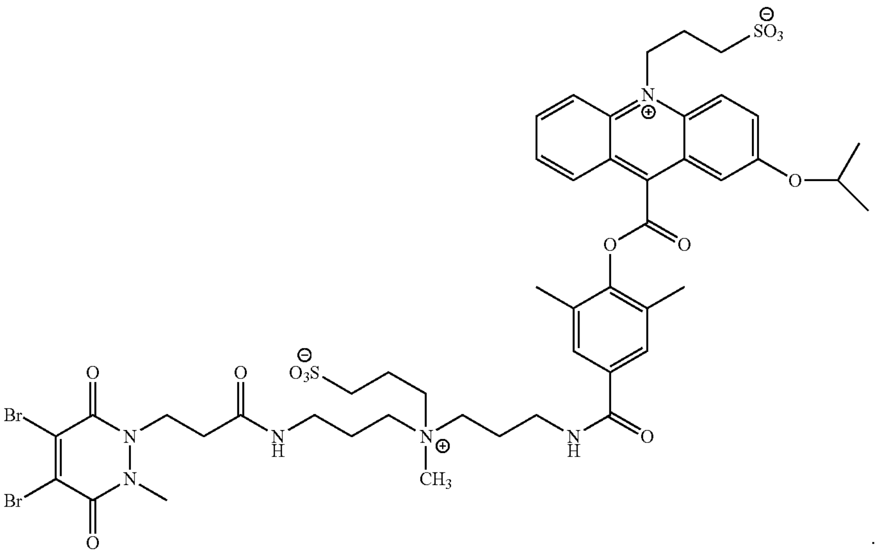

9. A conjugate, comprising:

an analyte-specific binder having at least one disulfide bond capable of reduction to two sulfhydryl groups; and at least one label of claim 1; and has the structure of Formula XII:

Formula XII

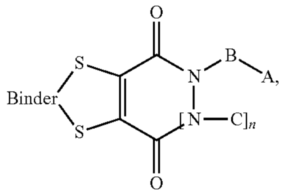

n = 1 or 0 wherein "Binder" represents the analyte-specific binder, and "A," "B," and "C" are as defined in claim 1;

wherein the analyte-specific binder is selected from the group consisting of a monoclonal antibody or analyte-binding fragment thereof, a polyclonal antibody or analyte-binding fragment thereof and an analyte-binding protein or analyte-binding fragment thereof.

10. The conjugate of claim 9, wherein the analyte-specific binder is a monoclonal antibody or analyte-binding fragment thereof, and wherein the at least one disulfide bond is in a hinge region of the monoclonal antibody or analyte-binding fragment thereof.

11. The conjugate of claim 10, wherein the monoclonal antibody or analyte-binding fragment thereof is an anti-CA 19-9 monoclonal antibody or analyte-binding fragment thereof.

12. The conjugate of claim 9, wherein the analyte-specific binder is selected from folate binding protein (FBP), FK-506 binding protein (FKBP), and VB12 intrinsic factor, or analyte-binding fragment thereof.

14. An immunoassay kit, comprising:

a first reagent comprising the conjugate of claim 9; and a second reagent comprising a solid phase having a second analyte-specific binder directly or indirectly attached thereto, wherein the second analyte-specific binder is specific for the analyte to which the analyte-specific binder of the conjugate binds; and wherein each of the analyte-specific binders of the first and second reagents specifically binds to an epitope of a target analyte to be detected by the immunoassay, and the epitopes do not substantially overlap, such that the analyte-specific binders of the first and second reagents can bind simultaneously to the same target analyte molecule.

15. A method of producing a conjugate of claim 9, the method comprising the steps of:

incubating an analyte-specific binder having at least one disulfide bond with at least one label of any one of claim 1 under conditions which reduce at least one disulfide bond of the analyte-specific binder to two sulfhydryl groups and directly or indirectly conjugates the at least one label to the two sulfhydryl groups of the analyte-specific binder and thereby produce the conjugate;

wherein the analyte-specific binder is selected from the group consisting of a monoclonal antibody or analyte-binding fragment thereof, a polyclonal antibody or analyte-binding fragment thereof and an analyte-binding protein or analyte-binding fragment thereof.

16. The method of claim 15, wherein the analyte-specific binder is a monoclonal antibody or analyte-binding fragment thereof, and wherein the at least one disulfide bond is in a hinge region of the monoclonal antibody or analyte-binding fragment thereof.

17. The method of claim 16, wherein the monoclonal antibody or fragment thereof is an anti-CA 19-9 monoclonal antibody or analyte-binding fragment thereof.

18. The method of claim 15, wherein the analyte-specific binder is selected from folate binding protein (FBP), FK-506 binding protein (FKBP), and VB12 intrinsic factor, or a analyte-binding fragment thereof.

19. The method of claim 15, wherein the conjugate comprises at least two labels directly or indirectly attached to the analyte-specific binder.

20. A method of detecting a target analyte in a sample, comprising the steps of:

combining a sample with the first and second reagents of the immunoassay kit of claim 14 to form a mixture;

incubating the mixture under conditions that allow for binding of the first reagent and the second reagent to target analyte present in the sample, thereby forming a complex; and detecting the complex.

* * * * *